United States Patent
Parker

(10) Patent No.: US 12,029,525 B2
(45) Date of Patent: Jul. 9, 2024

(54) REVERBERANT SHEAR WAVE FIELD ESTIMATION OF BODY PROPERTIES

(71) Applicant: University of Rochester, Rochester, NY (US)

(72) Inventor: Kevin Parker, Rochester, NY (US)

(73) Assignee: University of Rochester, Rochester, NY (US)

(*) Notice: Subject to any disclaimer, the term of this patent is extended or adjusted under 35 U.S.C. 154(b) by 1457 days.

(21) Appl. No.: 16/346,327

(22) PCT Filed: Nov. 3, 2017

(86) PCT No.: PCT/US2017/059875
§ 371 (c)(1),
(2) Date: Apr. 30, 2019

(87) PCT Pub. No.: WO2018/093584
PCT Pub. Date: May 24, 2018

(65) Prior Publication Data
US 2020/0054217 A1    Feb. 20, 2020

Related U.S. Application Data

(60) Provisional application No. 62/422,765, filed on Nov. 16, 2016.

(51) Int. Cl.
*A61B 8/00* (2006.01)
*A61B 5/00* (2006.01)
(Continued)

(52) U.S. Cl.
CPC .......... *A61B 5/0051* (2013.01); *A61B 5/0066* (2013.01); *A61B 5/055* (2013.01);
(Continued)

(58) Field of Classification Search
CPC ..... A61B 5/0051; A61B 5/0066; A61B 5/055; A61B 6/486; A61B 8/485; A61B 8/54;
(Continued)

(56) References Cited

U.S. PATENT DOCUMENTS 8,267,865 B2    9/2012 Hoyt et al.
10,327,739 B2 *  6/2019 Zheng ................ G01S 7/52022
(Continued)

FOREIGN PATENT DOCUMENTS

WO    2012/116364 A1    8/2012
WO    WO-2012116364 A1 *  8/2012    .......... A61B 5/0059
WO    WO-2016149480 A1 *  9/2016    .......... A61B 8/0883

OTHER PUBLICATIONS

Ormachea, Castaneda, Parker; Shear Wave Speed Estimation Using Reverberant Shear Wave Fields: Implementation and Feasibility Studies, Rec Aug. 9, 2017; rev Jan. 9, 2018; Final Jan. 12, 2019; Ultrasound in Med & Biology, vol. 44. No. 5; pp. 962-977 (Year: 2018).*

(Continued)

*Primary Examiner* — Joel Lamprecht
(74) *Attorney, Agent, or Firm* — Mark H. Jay

(57) ABSTRACT

A reverberant shear wave field in an object such as a patient's body or organ causes deformations in one or more selected directions measured with an imaging modality such as ultrasound or MR equipment or other imaging equipment, to estimate displacements in one or more selected directions over time increments and then viscoelastic properties such as stiffness or other parameters of the ROI.

25 Claims, 10 Drawing Sheets

(51) Int. Cl.
 *A61B 5/055* (2006.01)
 *A61B 6/00* (2006.01)
 *A61B 8/08* (2006.01)
(52) U.S. Cl.
 CPC .............. *A61B 6/486* (2013.01); *A61B 8/485* (2013.01); *A61B 8/54* (2013.01)
(58) Field of Classification Search
 CPC ..... A61B 5/0057; A61B 5/7239; A61B 8/085; A61B 6/12; A61B 6/502; A61B 6/5217; A61B 8/0825; G01R 33/56358
 See application file for complete search history.

(56) References Cited

U.S. PATENT DOCUMENTS

| | | | |
|---|---|---|---|
| 11,020,006 B2* | 6/2021 | Wang | A61B 6/032 |
| 2011/0130660 A1 | 6/2011 | Cloutier et al. | |
| 2012/0302883 A1 | 11/2012 | Kong et al. | |
| 2013/0004040 A1* | 1/2013 | Chen | G06T 11/005 382/131 |
| 2013/0058195 A1 | 3/2013 | Cloutier et al. | |
| 2013/0066204 A1* | 3/2013 | Fan | A61B 8/5223 600/438 |
| 2014/0046183 A1 | 2/2014 | Park et al. | |
| 2014/0316267 A1* | 10/2014 | Barry | A61B 8/0858 600/438 |
| 2015/0265249 A1 | 9/2015 | Urban et al. | |
| 2016/0213341 A1 | 7/2016 | Salcudean | |
| 2016/0242650 A1* | 8/2016 | Chen | A61B 5/0035 |
| 2018/0132831 A1* | 5/2018 | Yang | A61B 8/54 |
| 2019/0104963 A1* | 4/2019 | Kaditz | A61B 5/055 |
| 2021/0124042 A1* | 4/2021 | Fish | B06B 1/0207 |

OTHER PUBLICATIONS

Abramowitz M and Stegun I a 1964 Handbook of mathematical functions with formulas, graphs, and mathematical tables (Washington,: U.S. Govt. Print. Off.).
Baddour N 2011 Multidimensional wave field signal theory: mathematical foundations AIP Advances 1 0221201-02212024.
Bracewell R N 1965 the Fourier transform and its applications (New York: McGraw-Hill).
Brum J, Catheline S, Benech N and Negreira C 2015 Quantitative shear elasticity imaging from a complex elastic wavefield in soft solids with application to passive elastography IEEE Trans Ultrason Ferroelectr Freq Control 62 673-85.
Catheline S, Benech N, Brum J and Negreira C 2008 Time reversal of elastic waves in soft solids Physical review letters 100 064301.
Cook R K, Waterhouse R V, Berendt R D, Edelman S and Thompson M C 1955 Measurement of correlation coefficients in reverberant sound fields J Acoust Soc Am 27 1072-7.
Deffieux T, Gennisson J L, Bercoff J and Tanter M 2011 on the effects of reflected waves in transient shear wave elastography IEEE Trans Ultrason Ferroelectr Freq Control 58 2032-5.
Doyley M M 2012 Model-based elastography: a survey of approaches to the inverse elasticity problem Phys Med Biol 57 R35-R73.
Engel A J and Bashford G R 2015 A new method for shear wave speed estimation in shear wave elastography IEEE Trans Ultrason Ferroelectr Freq Control 62 2106-14.
Fai Y, Levinson S F, Dongshan F and Parker K J 1998 Feature-adaptive motion tracking of ultrasound image sequences using a deformable mesh IEEE Trans Med Imaging 17 945-56.
Fu D, Levinson S F, Graceswki S M and Parker K J 1999 Solution of the inverse problem in sonoelastography using an iterative forward approach. In: Ultrasonic Imaging and Tissue Characterization Symposium, pp. 61-62.
Gallot T, Catheline S, Roux P, Brum J, Benech N and Negreira C 2011 Passive elastography: shear-wave tomography from physiological-noise correlation in soft tissues IEEE Trans Ultrason Ferroelectr Freq Control 58 1122-6.

Hah Z, Hazard C, Mills B, Barry C, Rubens D and Parker K 2012 Integration of Crawling Waves in an Ultrasound Imaging System. Part 2: Signal Processing and Applications Ultrasound Med Biol 38 312-23.
Loupas T, Peterson R B and Gill R W 1995 Experimental evaluation of velocity and power estimation for ultrasound blood flow imaging, by means of a two-dimensional autocorrelation approach IEEE Trans Ultrason Ferroelectr Freq Control 42 689-99.
Manduca A, Lake D S, Kruse S A and Ehman R L 2003 Spatio-temporal directional filtering for improved inversion of MR elastography images Med Image Anal 7 465-73.
McLaughlin J and Renzi D 2006 Shear wave speed recovery in transient elastography and supersonic imaging using propagating fronts Inverse Probl 22 681-706.
Oliphant T E, Manduca A, Ehman R L and Greenleaf J F 2001 Complex-valued stiffness reconstruction for magnetic resonance elastography by algebraic inversion of the differential equation Magn Reson Med 45 299-310.
Parker K J 2013 Imaging in medical diagnosis and therapy, (Boca Raton, FL: CRC Press) pp. xvii, 331 p.
Parker K J, Doyley M M and Rubens D J 2011 Imaging the elastic properties of tissue: the 20 year perspective Phys Med Biol 56 R1-R29.
Parker K J and Lerner R M 1992 Sonoelasticity of organs: shear waves ring a bell J Ultrasound Med 11 387-92.
Parker K J and Maye B A 1984 Partially coherent radiation from reverberant chambers J Acoust Soc Am 76 309-13.
Parker K J, Taylor L S, Gracewski S and Rubens D J 2005 a unified view of imaging the elastic properties of tissue J Acoust Soc Am 117 2705-12.
Pengfei S, Heng Z, Manduca A, Urban M W, Greenleaf J F and Shigao C 2012 Comb-push ultrasound shear elastography (CUSE): a novel method for two-dimensional shear elasticity imaging of soft tissues IEEE Trans Med Imaging 31 1821-32.
Pierce A D 1981 McGraw-Hill series in mechanical engineering, (New York: McGraw-Hill Book Co.).
Ringleb S I, Chen Q, Lake D S, Manduca A, Ehman R L and An K N 2005 Quantitative shear wave magnetic resonance elastography: comparison to a dynamic shear material test Magn Reson Med 53 1197-201.
Romano A J, Bucaro J A, Ehnan R L and Shirron J J 2000 Evaluation of a material parameter extraction algorithm using MRI-based displacement measurements IEEE Trans Ultrason Ferroelectr Freq Control 47 1575-81.
Roux P, Sabra K G, Kuperman W A and Roux A 2005 Ambient noise cross correlation in free space: theoretical approach J Acoust Soc Am 117 79-84.
Sinkus R, Lorenzen J, Schrader D, Lorenzen M, Dargatz M and Holz D 2000 High-resolution tensor MR elastography for breast tumour detection Phys Med Biol 45 1649-64.
Taylor L S, Porter B C, Rubens D J and Parker K J 2000 Three-dimensional sonoelastography: principles and practices Phys Med Biol 45 1477-94.
Tzschatzsch H, Guo J, Dittmann F, Hirsch S, Barnhill E, Johrens K, Braun J and Sack I 2016 Tomoelastography by multifrequency wave number recovery from time-harmonic propagating shear waves Med Image Anal 30 1-10.
Tzschatzsch H, Ipek-Ugay S, Guo J, Streitberger K J, Gentz E, Fischer T, Klaua R, Schultz M, Braun J and Sack I 2014 In vivo time-harmonic multifrequency elastography of the human liver Phys Med Biol 59 1641-54.
Tzschatzsch H, Ipek-Ugay S, Trong M N, Guo J, Eggers J, Gentz E, Fischer T, Schultz M, Braun J and Sack I 2015 Multifrequency time-harmonic elastography for the measurement of liver viscoelasticity in large tissue windows Ultrasound Med Biol 41 724-33.
Van Houten E E, Miga M I, Weaver J B, Kennedy F E and Paulsen K D 2001 Three-dimensional subzone-based reconstruction algorithm for MR elastography Magn Reson Med 45 827-37.
Castaneda et al., Prostate Cancer Detection Using Crawling Wave Sonoelastography, Medical Imaging 2009: Ultrasonic Imaging and Signal Processing, edited by Stephen A. McAleavey, Jan D'hooge Proc. of SPIE vol. 7265, 726513-1-726513-10.

(56) References Cited

OTHER PUBLICATIONS

Zhang et al., Congruence of Imaging Estimators and Mechanical Measurements of Viscoelastic Properties of Soft Tissues, Ultrasound in Med. & Biol., vol. 33, No. 10, pp. 1617-1631, 2007.
International Search Report dated Feb. 26, 2018 in connection with International application No. PCT/US2017/059875.
Informal Comments submitted Apr. 26, 2018 by Applicant on WO-ISA in connection with International application No. PCT/US2017/059875.

* cited by examiner

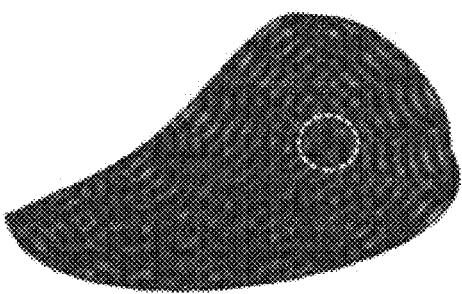
FIG. 3F
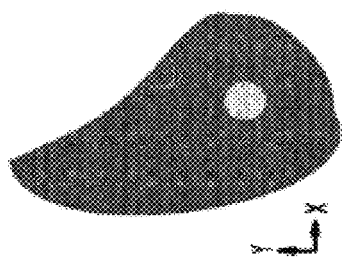
FIG. 3C
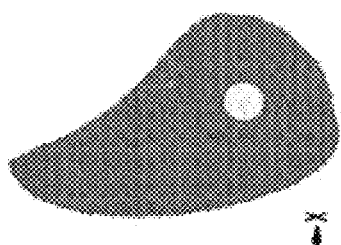
FIG. 3B
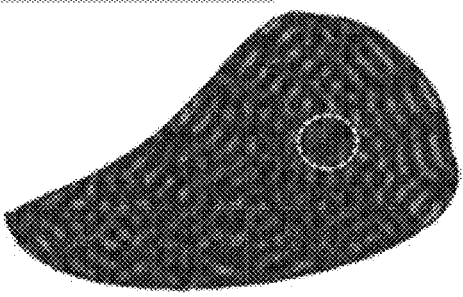
FIG. 3E
FIG. 3A
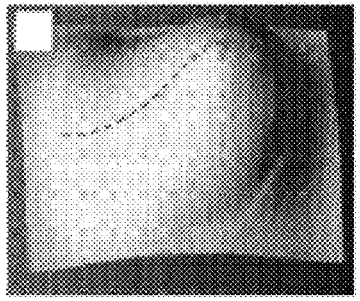
FIG. 3D
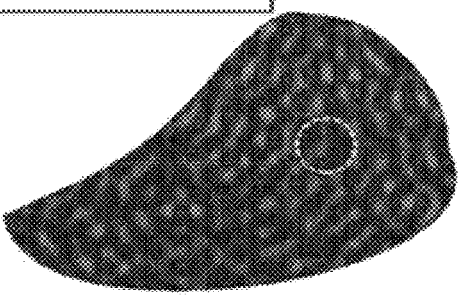
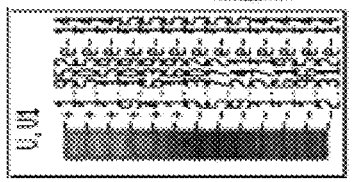

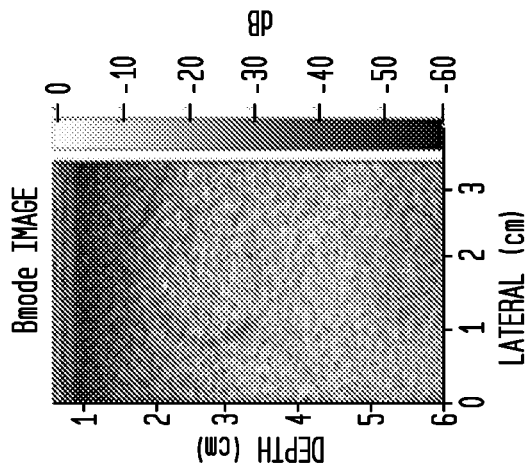
FIG. 8A
FIG. 8B
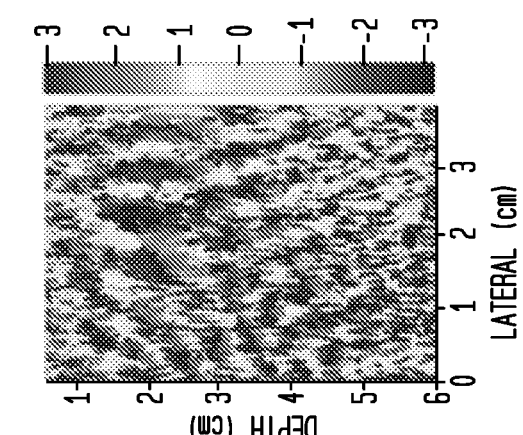
FIG. 8C
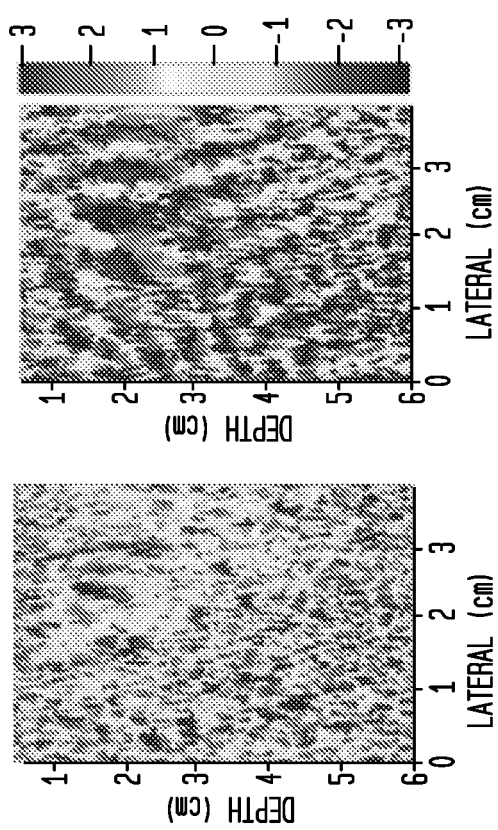
FIG. 8D
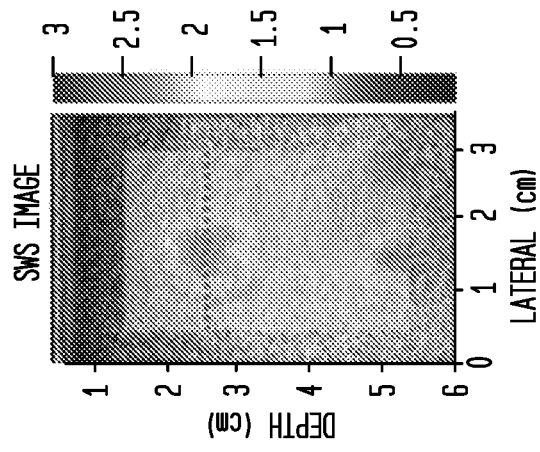
FIG. 8E
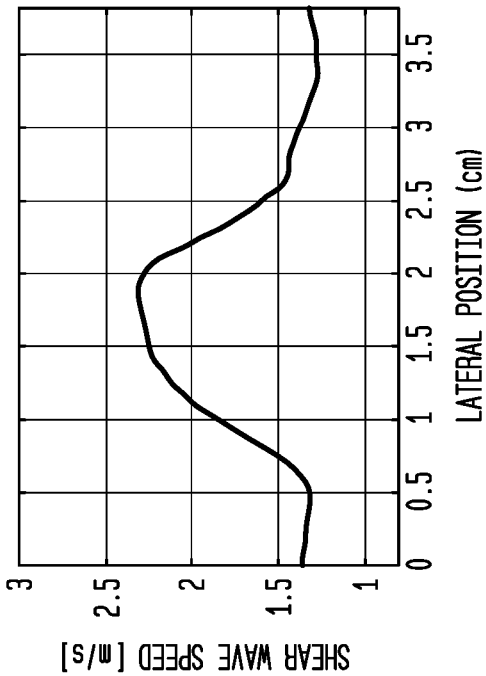

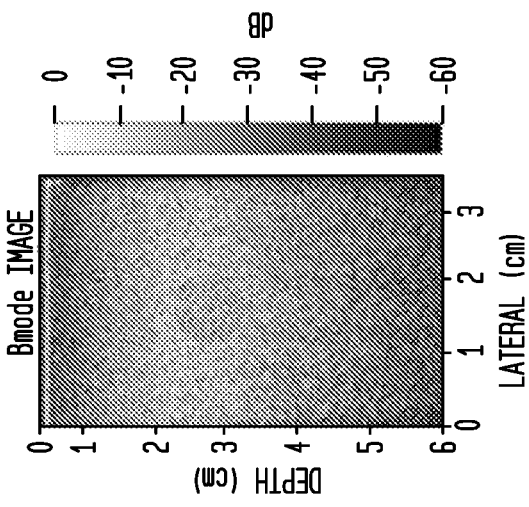
FIG. 9A
FIG. 9B
FIG. 9C
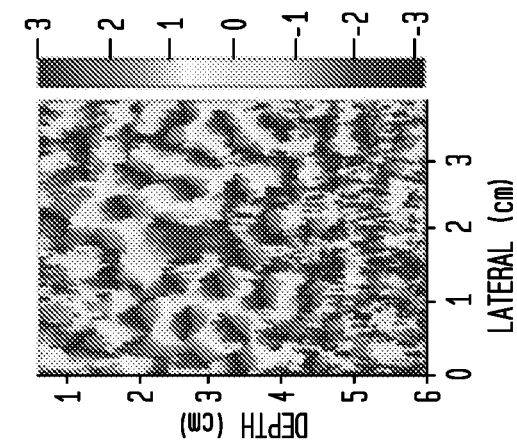
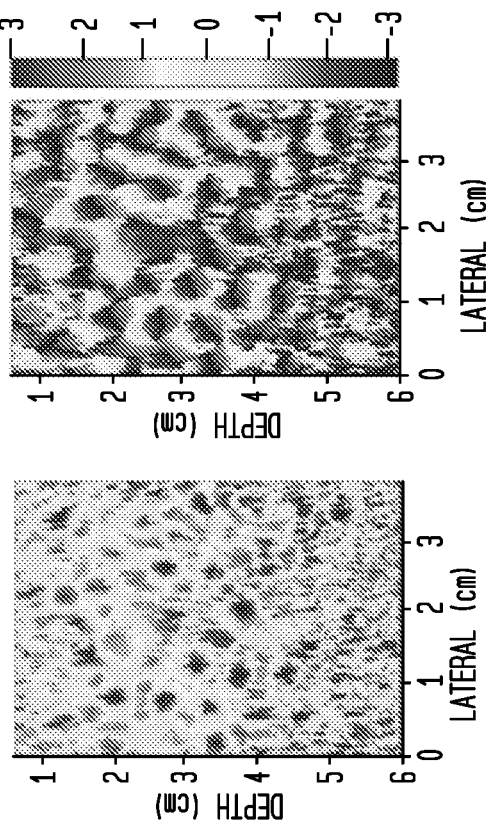
FIG. 9D
FIG. 9E
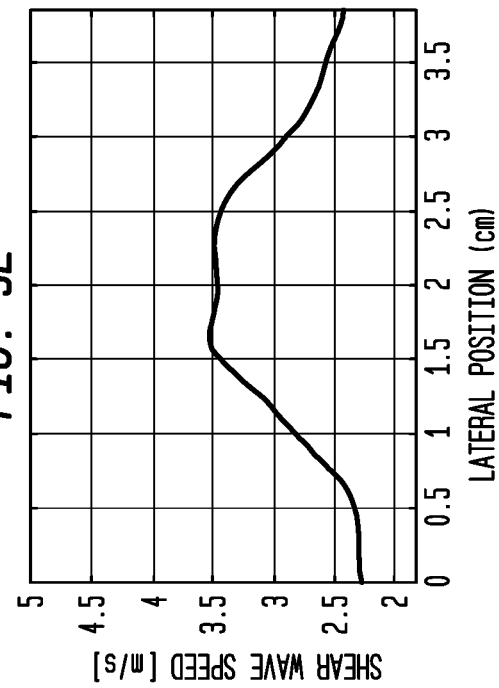
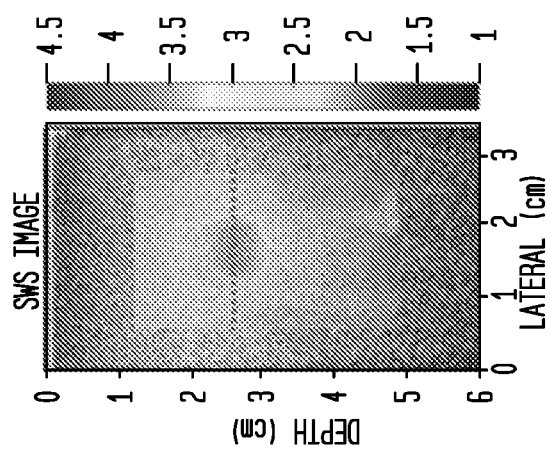

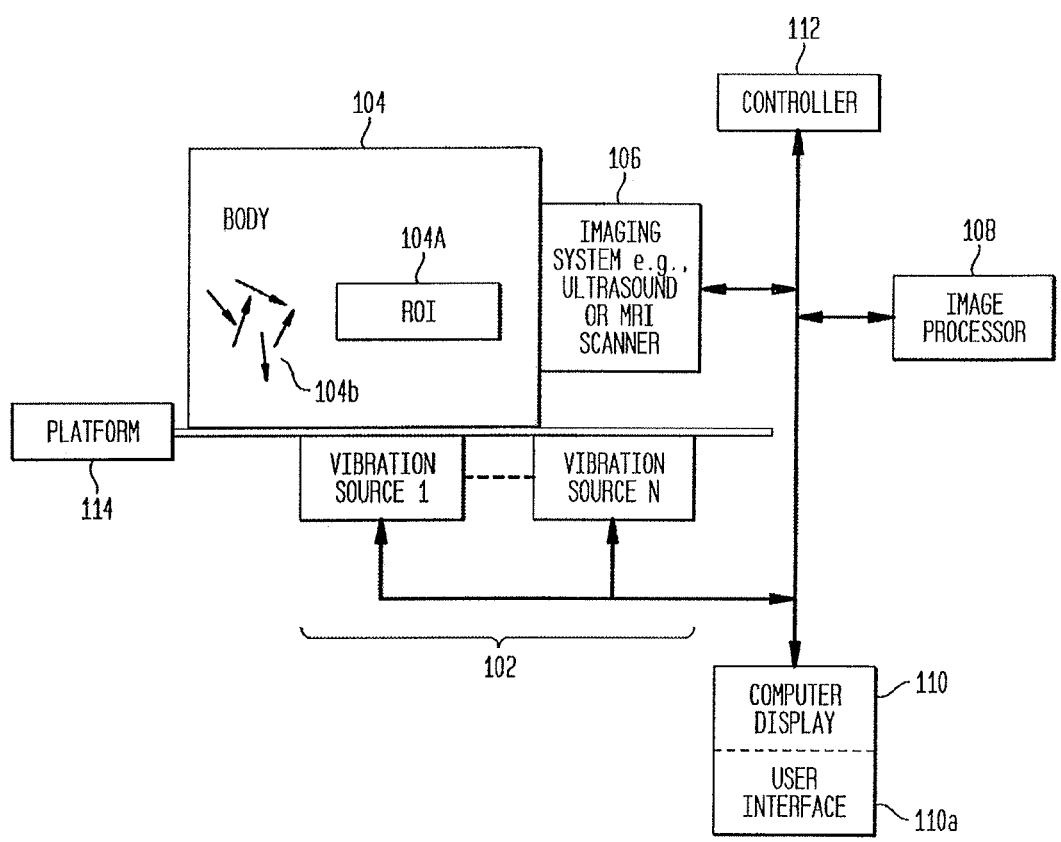

REVERBERANT SHEAR WAVE FIELD ESTIMATION OF BODY PROPERTIES

CROSS-REFERENCE TO PRIOR APPLICATIONS

This application is a § 371 national stage of PCT International Application No. PCT/US2017/059875, filed Nov. 3, 2017, which claims priority to U.S. Provisional Application Ser. No. 62/422,765 filed on Nov. 16, 2016, the contents of each of which are hereby incorporated by reference herein in their entirety.

FIELD

This patent application relates to systems and methods for estimating viscoelastic properties such as elasticity and stiffness of internal body structures, for example lesions in a patient.

BACKGROUND

Elastography has been used in recent times to estimate biomechanical properties such as stiffness of a region of interest (ROI) in a patient, for example to assess the stiffness of a mass in a breast of abdomen as an aid in deciding if the mass is benign or cancerous or to determine other characteristics of the lesion. In principle, a force is applied to the ROI and the way the ROI deforms or moves in response, as measured by an imaging modality such as ultrasound or MM, is used as an indication of stiffness. The known techniques include (a) quasistatic elastography, in which the change in shape of a region of interest and its surroundings due to compression is measured, (b) acoustic radiation force impulse imaging (ARFI), in which the way a focused ultrasound beam pushes the ROI along the beam direction is used as a measure of stiffness, (c) shear wave elasticity imaging (SWEI), which is similar to ARFI but the ROI displacement normal to the beam direction is the measure of stiffness, and (d) supersonic shear imaging (SSI), in which acoustic radiation force pushing the ROI generates shear waves and the speed of those waves is a measure of stiffness. In magnetic resonance elastography, the speed of shear waves in the patient is used as a stiffness measure.

In the more detailed discussion of background below, and in the description of the new approaches, references are identified in parenthesis; full citations of the references are provided at the end of the specification. All cited referenced material are hereby incorporated by reference.

There has been a robust development of techniques to estimate and image the biomechanical properties of tissues (Parker et al., 2011). The applied stimulus can be quasi-static, transient, or continuous waves. Each one of these has unique mathematics and techniques for inverse solutions (Doyley, 2012), but all lie on a continuum of biomechanical responses (Parker et al., 2005; Parker, 2013). Shear wave propagation has received significant attention, but an inherent challenge in many approaches is the presence of reflected waves from organ boundaries and internal inhomogeneities. These reflections are responsible for modal patterns (Parker and Lerner, 1992; Taylor et al., 2000) in continuous wave applications and also for backwards travelling waves in transient experiments (Ringleb et al., 2005). Directional filtering can be used to eliminate some types of reflections (Pengfei et al., 2012; McLaughlin and Renzi, 2006; Deffieux et al., 2011; Manduca et al., 2003; Engel and Bashford, 2015; Hah et al., 2012).

Continuous shear wave inversion approaches have been developed to estimate the unknown tissue stiffness. They include inversions of the Helmoltz equation in magnetic resonance elastography (MRE) (Van Houten et al., 2001; Ringleb et al., 2005; Romano et al., 2000; Sinkus et al., 2000; Oliphant et al., 2001) and sonoelastography (Parker and Lerner, 1992; Fai et al., 1998; Fu et al., 1999). Another class of estimations has been developed for underwater acoustics and geomechanics using random signals (Roux et al., 2005) and has been extended to noise correlation measurements in soft tissues (Gallot et al., 2011; Catheline et al., 2008; Brum et al., 2015). These involve spatial coherence of noise functions measured at two points, and can be recast as Green's functions and time reversal solutions. An approach using a mechanical vibration source to produce multiple wave directions in a large organ such as the liver, has been developed by Tzschatzsch et al. (2014; 2015; 2016). Using a probability approach, they characterize the shear wave speed by finding the minimum wavenumber as a function of direction.

While the known techniques can be useful and beneficial, a need still remains for new approaches to estimating properties such as stiffness of a region of interest in a body that can provide improved performance and results. For example, there is a need for more effective ways to measure stiffness of regions of interest deeper in a patient, such as deep in the abdomen, and particularly in obese patients. There also is a need to reduce undesirable effects of acoustic energy interactions with tissue other than the region of interest. And, there is a need to generally improve performance and reduce the cost of equipment and its operation. This patent specification describes such new approaches.

SUMMARY

This patent specification describes new approaches to measuring and estimating elastic properties of regions of interest or anatomical organ inside a body. The general framework involves using reverberant shear waves in bounded elastic media.

A non-limiting example of a system using a reverberant shear wave field in a body to measure viscoelastic properties of hidden regions of interest in the body comprises a plurality of vibration sources configured to produce shear waves at a selected frequency that interact with each other and with structures in the body to produce the desired reverberant shear wave field, an imaging device configured to measure motion of the region of interest in the body in a first selected direction in the presence of said reverberant shear wave field and to produce an estimate of the measured motion, an image processor configured to receive as inputs the selected frequency of the shear waves and said estimate of measured motion and to process the inputs with computer algorithms to provide an estimate of one or more viscoelastic properties of said region of interest in the body, a computer display configured to display said estimate of one or more viscoelastic properties of the region of interest, and a controller operatively coupled with said vibration sources, imaging device, and computer display to control their operation.

The imaging device can be an ultrasound scanner that includes an ultrasound transducer configured to provide a time sequence of ultrasound images of the region of interest and the estimate of measured motion. As another example, the imaging device can be a magnetic resonance imaging (MM) machine configured to provide a time sequence of magnetic resonance images of the region of interest and the estimate of measured motion. Other examples of an imaging device include an x-ray imaging device that takes a rapid succession of x-ray images of the region of interest, and an Optical Coherence Tomography (OCT) device that similarly takes a rapid sequence of images. The vibration sources can be configured to produce shear waves that have substantially the same frequency, or are within the same range that in turn is within a wider range of, for example, 30-1000 Hz or more, such as 1600-2400, and an even wider range such as 1000-4000 Hz. In one example, 3-7 individual vibration sources can be used, but more than 7 can be used in other examples.

The estimate of measured motion includes a position in the selected direction of the region of interest at plural respective times and speed of the change in position in that direction. The image processor can be configured to calculate one or more estimates of the motion and speed as a function of auto-correlation of the positions of the ROI at respective times. The system can be further configured to measure motion and provide an estimate of the measured motion in one or two additional directions, in which case a map can be produced to show a spatial distribution of one or more viscoelastic parameters such as stiffness in a plane in 2D or a volume in 3D.

BRIEF DESCRIPTION OF THE DRAWING

FIG. 3(a), illustrates a simulation of a 3D mesh of a breast model, FIG. 3(b) illustrates a simulation of a geometrical model of the breast shaped as a 2D profile of the mesh model in FIG. 3(a) with boundary conditions and loads indicated in Abaqus/CAE, FIG. 3(c) illustrates a simulation of a finite shell-element mesh of FIG. 3(b) with material properties definition in the background and inclusion (diameter=17 mm) and delimitation of the region of interest, and FIG. 3(d), FIG. 3(e), and FIG. 3(f)[-f)] illustrate simulations of a displacement field in the x-axis for the frequencies of operation on 400 Hz, 500 Hz, and 600Hz, respectively.

FIG. 8 consists of portions (a) through (e), where (a) illustrates a displacement pattern at 400 Hz obtained for a gelatin phantom, (b) illustrates a phase map of (a), (c) is a B-mode ultrasound image, portions (d) is an SWS map calculated from (a) using a second moment algorithm where the dotted line illustrates the depth of the SWS profile, and (e) illustrates an SWS profile across a lesion.

FIG. 9 consists of portions (a) through (e), where (a) illustrates a displacement pattern at 450 Hz, applied to a zerdine breast phantom, (b) is a phase map of (a), (c) is a B-mode ultrasound image, (d) is an SWS map calculated from (a) using a second moment algorithm at 450 Hz where the dotted line illustrates the location of the SWS profile, and (e) is an SWS profile at a fixed depth through a lesion across the lateral direction from (d).

FIG. 11 illustrates main elements of a system using a reverberant shear wave field in a body to estimate properties of regions of interest such as stiffness.

DETAILED DESCRIPTION OF EXAMPLES OF EMBODIMENTS

A detailed description of examples of preferred embodiments is provided below. While several embodiments are described, the new subject matter described in this patent specification is not limited to any one embodiment or combination of embodiments described herein, but instead encompasses numerous alternatives, modifications, and equivalents. In addition, while numerous specific details are set forth in the following description to provide a thorough understanding, some embodiments can be practiced without some of these details. Moreover, for clarity and conciseness, certain technical material that is known in the related art has not been described in detail in order to avoid unnecessarily obscuring the new subject matter described herein. It should be clear that individual features of one or several of the specific embodiments described herein can be used in combination with features or other described embodiments. Further, like reference numbers and designations in the various drawings indicate like elements.

First, a discussion is presented of a theoretical basis for the new approaches to estimating stiffness of an internal ROI, and then examples of specific implementations are described.

Figure 1:
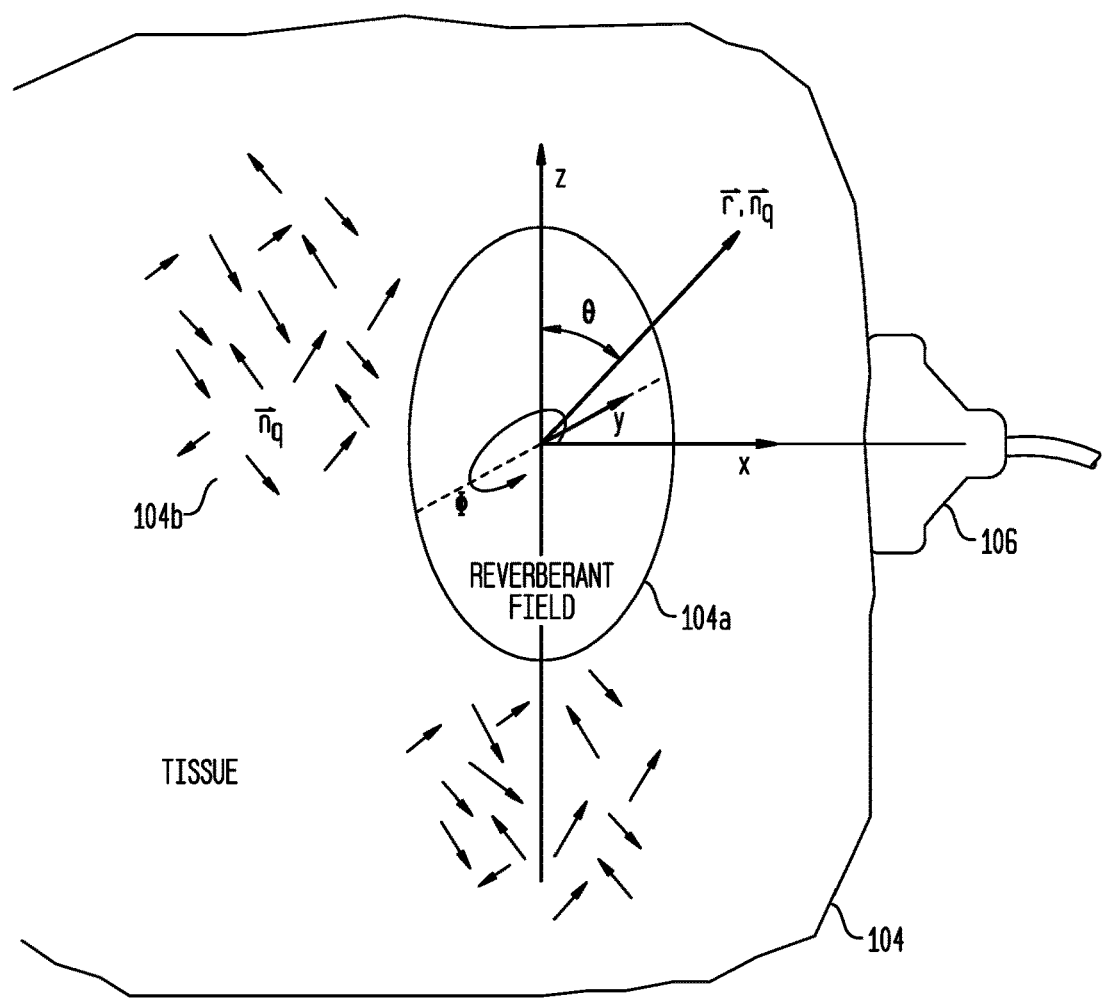
FIG. 1 illustrates the orientation of an imaging transducer and an object that has an isotropic random distribution of shear waves propagating through its interior, consistent with a theory of reverberant shear wave fields. The x-axis of the coordinate system is aligned with the axial direction of the imaging transducer, and it is assumed that the imaging system detects motion in the x-direction. The $\vec{n}_q$ are the direction vectors of the individual plane waves that are distributed throughout the reverberant interior.

FIG. 1 illustrates a geometry and a coordinate system that might help in appreciating the discussion below. The figure shows an imaging transducer 106 and an object 104 that has an isotropic random distribution of shear waves propagating through its interior, represented by the $\vec{n}_q$ direction vectors 104b of the individual plane waves that are distributed throughout the reverberant interior and in the region of interest 104a, consistent with a theory of reverberant shear wave fields. The x-axis of the coordinate system is aligned with the axial direction of the imaging transducer 106, and it is assumed that the imaging system detects motion in the x-direction.

The complex pressure $\hat{P}$ at a position ε in a reverberant chamber can be thought of as the superposition of plane waves incident from all directions (Pierce, 1981; Parker and Maye, 1984)

$$\hat{P}(t, \varepsilon) = \sum_q \hat{P}_q \exp[j(kn_q \cdot \varepsilon - \omega_0)t], \quad (1)$$

where the index q represents direction, $n_q$ are unit vectors uniformly distributed around $4\pi$ solid angle, k and ω are the wave number and radial frequency of the plane waves, and $\hat{P}_q$ are independent, identically distributed variables of random magnitude and phase. The corresponding velocity at a point is thereby given as $$v(t, \varepsilon) = \sum_q n_q \hat{v}_q \exp[j(kn_q \cdot \varepsilon - \omega_0 t)], \quad (2)$$

Where, from the plane-wave impedance relations, $$\hat{v}_q = n_q \hat{P}_q / \rho c, \quad (3)$$

where ρ is the media density, and c the speed of sound.

To calculate the autocorrelation function, the x component of velocity at some position ε within the tissue can be written as:

$$\hat{v}_x(\varepsilon) = e_x \cdot v(\varepsilon) = \sum_q n_{xq} \hat{v}_q \exp[j(kn_q \cdot \varepsilon - \omega_0 t)], \quad (4)$$

where $\hat{e}_x$ is a unit vector in the x direction and $$n_{xq} = n_q \cdot \hat{e}_x. \quad (5)$$

The summation on q is understood to be taken over $4\pi$ solid angle.

Writing the correlation function definition then substituting equation (4), gives:

$$B_{v_x v_x}(\Delta t, \Delta \varepsilon) = \quad (6)$$

$$E\{\hat{v}_x(t, \varepsilon)\hat{v}_x^*(t+\Delta t, \varepsilon+\Delta \varepsilon)\} = E\left\{\left(\sum_q n_{xq} \hat{v}_q \exp[j(kn_q \cdot \varepsilon - \omega_0 t)]\right) \times \right.$$

$$\left. \left(\sum_{q'} n_{xq'} \hat{v}_{q'}^* \exp\{-j[kn_{q'} \cdot (\varepsilon + \Delta \varepsilon) - \omega_0(t+\Delta t)]\}\right)\right\}$$

where E{ } represents an ensemble average and the asterisk represents conjugation. The product of the two series will include cross terms of the form:

$$E\{n_{xq} \hat{v}_q n_{xq'} \hat{v}_{q'} e^{(\cdots)}\} \quad (7)$$

But since the $n_{xq}$ and $\hat{v}_q$ are independent and the $\hat{v}_q$ are uncorrelated, this term vanishes. Thus:

$$B_{v_x v_x}(\Delta t, \Delta \varepsilon) = E\left\{\sum_q n_{xq}^2 v_q^2 \exp[j(\omega_0 \Delta t - kn_q \cdot \Delta \varepsilon)]\right\}. \quad (8)$$

Taking the real part of the equation (8), gives:

$$B_{v_x v_x}(\Delta t, \Delta \varepsilon) = (V^2)_{avg} E\left\{\sum_q n_{xq}^2 \cos(\omega_0 \Delta t - kn_q \cdot \Delta \varepsilon)\right\}, \quad (9)$$

where, since the $V_q$ are independent of the $n_{qx}$ and cosine terms, the mean squared value of the velocity is taken out from the curly braces. Since an ideal, diffuse field is assumed to be present in the reverberant chamber, then the ensemble or spatial averaging will assign equal weighting to all directions of incident sound. Thus, the average of the summation over discrete directions becomes the average over all directions of incident waves (Pierce, 1981; Cook et al., 1955), around the polar coordinates of FIG. 1:

$$B_{v_x v_x}(\Delta t, \Delta \varepsilon) = \frac{(V^2)_{avg}}{2\pi} \int_{hemisphere} n_{xq}^2 \cos(\omega_0 \Delta t - kn_q \cdot \Delta \varepsilon) d\Omega. \quad (10)$$

Without loss of generality, vector Δε can be aligned with the z axis in FIG. 1. Using spherical coordinates:

$$n_q \cdot \Delta \varepsilon_z = \Delta \varepsilon_z \cos \theta, \text{ and} \quad (11)$$

$$(n_{xq})^2 = (n_q \cdot \hat{e}_x)^2 = (\sin \theta \cos \theta)^2, \quad (12)$$

and the differential solid angle is $$d\Omega = \sin\theta d\theta d\phi, \text{ so} \quad (13)$$

$$B_{v_x v_x}(\Delta t, \Delta \varepsilon_z) = \quad (14)$$

$$\frac{(V^2)_{avg}}{2\pi} \int_{\phi=0}^{2\pi} \int_{\theta=0}^{\pi} (\sin\theta\cos\phi)^2 \times \cos(\omega_0 \Delta t - k\Delta\varepsilon_z \cos\theta)\sin\theta d\theta d\phi.$$

Integrating first over $\phi$ and expanding the cosine term yields $$= 2\pi(V^2)_{avg}\left(\frac{j_1(k\Delta\varepsilon_z)}{k\Delta\varepsilon_z}\right)\cos\omega_0\Delta t \tag{15}$$

where $j_1(x)$ is the spherical Bessel function of the first kind, of order 1. This result is commensurate with the role of spherical Bessel functions in solutions to the Helmholtz equation via Fourier and Hankel transformations (Baddour, 2011). Also, equation (15) can be written in terms of trigonometric functions or Bessel functions of order 3/2 (Parker and Maye, 1984; Abramowitz and Stegun, 1964).

Now, switching to shear waves, the major difference is that the direction of propagation is perpendicular to the direction of displacement. Thus, if $n_q$ is taken as the direction of propagation, $n_{qp}$ is a perpendicular direction of shear displacement and velocity. Therefore, $n_q \cdot n_{qp}=0$.

To account for the perpendicular relation in the case of shear wave, 90° or $\pi/2$ is added to the angle formed by q and x (the detected direction). Thus, equation (12) becomes $$(n_{xqp})^2 = (n_{qp}\cdot\hat{e}_x)^2 = \left(\sin\left(\theta+\frac{\pi}{2}\right)\cos\phi\right)^2 = (\cos\theta)^2(\cos\phi)^2, \tag{16}$$

and, following the same logical progression as before, equation (14) becomes $$Bv_xv_x(\Delta t, \Delta\varepsilon_z) = \frac{(V^2)_{avg}}{2\pi}\int_{\phi=0}^{2\pi}\int_{\theta=0}^{\pi}(\cos\theta)^2(\cos\phi)^2 \times \tag{17}$$
$$\cos(\omega_0\Delta t - k\Delta\varepsilon_z\cos\theta)\sin\theta d\theta d\phi$$
$$= (V^2)_{avg}\left(\cos(\omega_0 t)\left[\frac{\sin(k\Delta\varepsilon_z)}{k\Delta\varepsilon_z} - \frac{2j_1(k\Delta\varepsilon_z)}{k\Delta\varepsilon_z}\right]\right).$$

In the case where $\Delta\varepsilon$ is taken along the x-axis (the direction of the detected velocity), then $n_q\cdot\hat{e}_x\Delta\varepsilon_x=\Delta\varepsilon_x \sin\theta\cos\theta$, the argument in equation (17) becomes $\cos(\omega_0\Delta t-k\Delta\varepsilon_x \sin\theta\cos\theta)$, and the integration results in $$Bv_xv_x(\Delta t, \Delta\varepsilon_x) = 2(V^2)_{avg}\cos(\omega_0 t)\left[\frac{j_1(k\Delta\varepsilon_x)}{k\Delta\varepsilon_x} + \frac{\sin(k\Delta\varepsilon_x)}{k^3\Delta\varepsilon_x^3} - \frac{1}{k^2\Delta\varepsilon_x^2}\right]. \tag{18}$$

Figure 2:
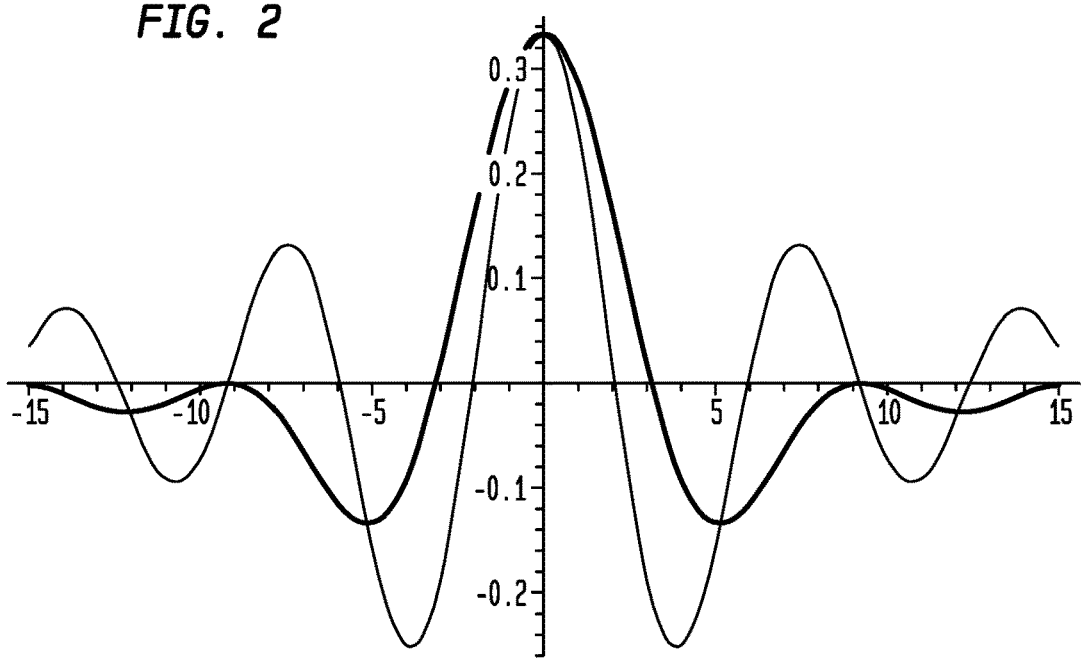
FIG. 2 illustrates that autocorrelation $B_{vv}(t=0, \Delta\varepsilon)$ depends on the relative direction of $\Delta\varepsilon$ with respect to the detected component of the velocity vector. In this case, the detected direction of motion is taken as the x-axis. The thick line gives the autocorrelation with respect to x, the thin line shows the autocorrelation when $\Delta\varepsilon$ is taken in the perpendicular z-direction. The wavenumber k is set to unity for these curves.

The two functions from equations (17) and (18) are shown in FIG. 2, which illustrates that autocorrelation $B_{vv}(t=0, \Delta\varepsilon)$ depends on the relative direction of $\Delta\varepsilon$ with respect to the detected component of the velocity vector. In this case, the detected direction of motion is taken as the x-axis. The thick line gives the autocorrelation with respect to x, the thin line shows the autocorrelation when $\Delta\varepsilon$ is taken in the perpendicular z-direction. The wavenumber k is set to unity for these curves.

The simplicity of equations (17) and (18), basically "sinc" and "jinc" spatial functions, is useful for practical implementations. An ultrasound or magnetic resonance imaging (MRI) scanner can track tissue motion within a region of interest. This generates a function v(x) along some region of interest (ROI). The tissue is subjected to multiple shear wave sources that are operating at a frequency typically in the range of 30-1000 Hz. The correlation function $B_{vv}$ is calculated and fit to equation (17) or (18) to estimate the unknown parameter k. Local estimates of k are used to create a map, typically displayed in color, representing the shear wave speed and hence the stiffness of the tissue at different locations.

An efficient estimator for the unknown k in equation (17) is realized by examining the Fourier transform of the autocorrelation function:

$$\mathfrak{J}_x\left\{\frac{\sin(kx)}{kx} - \frac{2j_1(kx)}{kx}\right\} = \sqrt{\frac{\pi}{2}}\left(\frac{s^2}{k^3}\right) \text{ for } s \leq k, \tag{19}$$

where s is the spatial transform variable. This is a strictly bandlimited function with upper limit of spatial frequency set by k, the unknown wavenumber. The second moment $m^2$ of the transform is therefore similarly determined by k. From Bracewell, chapter 8, page 143 (1965):

$$m_s^2 = \int_{-k}^{+k}(s^2)\sqrt{\frac{\pi}{2k^3}}\left(\frac{s^2}{2k^3}\right)ds \tag{20}$$
$$= \frac{\sqrt{2\pi}}{5}k^2.$$

Similarly, the Fourier transform of equation (18)'s spatial term is:

$$\mathfrak{J}_x = \{\cdot\} = \frac{s(s-k)}{2k^3} \text{ for } 0 < s < k, \tag{21}$$

and the function is a real and even function of s. The second moment for this case is:

$$m_s^2 = \frac{k^2}{5}. \tag{22}$$

Furthermore, it is well known that the second moment of a transform is precisely related to the second derivative of the function at the origin (Bracewell, 1965). This can be approximated by a finite difference. Thus:

$$|\hat{k}|^2 \cong C[\text{Re}\{Bvv(\Delta x)\} + \text{Re}\{Bvv(-\Delta x)\} - 2\text{Re}\{Bvv(0)\}], \tag{23}$$

where $\hat{k}$ is the estimate, C is a constant inversely dependent on $\Delta x^2$, and the $\Delta x$ lag and zero lag values of the real part of the autocorrelation at $\Delta t=0$ from some segment of data are used. A similar expression applies to the estimate using $\Delta z$.

The new approaches described in this patent specification have been confirmed through numerical simulations discussed below.

Numerical simulations using finite elements analysis have been conducted using Abaqus/CAE version 6.14-1 (Dassault Systems, Vélizy-Villacoublay, France) in order to corroborate gelatin phantom experiments (shell-element analysis), and breast phantom (3D solid finite element analysis) described further below in this patent specification.

FIG. 3 illustrates simulations where (a) shows a 3D mesh of a breast model, (b) shows a geometrical model of the breast shaped as a 2D profile of the mesh model in (a) with boundary conditions and loads indicated in Abaqus/CAE, (c) shows a finite shell-element mesh of (b) with material properties definition in the background and inclusion (diameter=17 mm), and delimitation of the region on interest, and (d-f) shows a displacement field in the x-axis for the frequencies of operation: 400 Hz, 500 Hz, and 600 Hz, respectively.

In Shell-element analysis, the profile of a 3D mesh model of a breast (FIG. 3(a)) is used to create a 2D geometrical solid model of a homogeneous breast with a hard inclusion simulating a tumor. The boundary conditions were set to have eight surface traction loads located in distinct parts of the breast model in order to produce shear displacement at the frequency of operation (FIG. 3(b)). The model was meshed using approximately 1,500,000 hybrid and quadratic shell elements (FIG. 3(c)). Power law frequency dependent viscoelastic material properties were chosen to represent tissue. The elastic modulus, density, and viscoelastic parameters assigned to the background and the inclusion are described in Table 1. These parameters are in the range of gelatin phantom values extracted using the mechanical testing described below. The type of simulation was selected to be steady-state dynamic direct solution for a range of frequencies between 100 Hz and 1000 Hz. This type of analysis calculates the 3D complex sinusoidal steady state solution of displacement and particle velocity of the breast when the defined loads introduce vibrations in the model.

TABLE 1

Viscoelastic material parameters of the background and inclusion in the 2D finite element model. The power law frequency-dependent model is $g^*(\omega) = g_1^* f^{-a}$, where $g^*(\omega)$ is the Fourier transform of the non-dimensional shear relaxation function, $g_1^*$ is a complex constant, a is a real constant, and $f = \omega/2\pi$.

| | Density, $\rho$ (kg/m³) | Poisson's ratio, $\nu$ | Young's modulus E (Pa) | Power law frequency-dependent parameters | | |
|---|---|---|---|---|---|---|
| | | | | Real $\{g_1^*\}$ | Imag $\{g_1^*\}$ | a |
| Background | 998 | 0.499 | 5,227.2 | 0.01730 | −0.1715 | 0.936 |
| Inclusion | 998 | 0.499 | 18,154.8 | | | |

After the simulation was conducted, the complex values of particle velocity were stored for a posterior post-processing step. FIG. 3(d-f) shows reverberant vector fields within the background and inclusion for different frequencies.

In 3D solid finite element analysis, a 3D geometrical solid model of a homogeneous breast with a hard inclusion was created and meshed using approximately 400,000 hybrid and quadratic tetrahedral elements using the shape of the mesh model in FIG. 3(a). The material properties were chosen according to the specifications of the zerdine breast phantom (model 509, CIRS Inc., Norfolk, Va.) assigned to the background and inclusion part as described in Table 2.

TABLE 2

Viscoelastic material parameters of the background and inclusion in the 3D finite element model. The power law frequency-dependent model is $g^*(\omega) = g_1^* f^{-a}$, where $g^*(\omega)$ is the Fourier transform of the non-dimensional shear relaxation function, $g_1^*$ is a complex constant, a is a real constant, and $f = \omega/2\pi$.

| | Density, $\rho$ (kg/m³) | Poisson's ratio, $\nu$ | Young's modulus E (Pa) | Power law frequency-dependent parameters | | |
|---|---|---|---|---|---|---|
| | | | | Real $\{g_1^*\}$ | Imag $\{g_1^*\}$ | a |
| Background | 998 | 0.499 | 20,000 | 0.004521 | −0.04482 | 0.936 |
| Inclusion | 998 | 0.499 | 40,000 | | | |

Figure 4A:
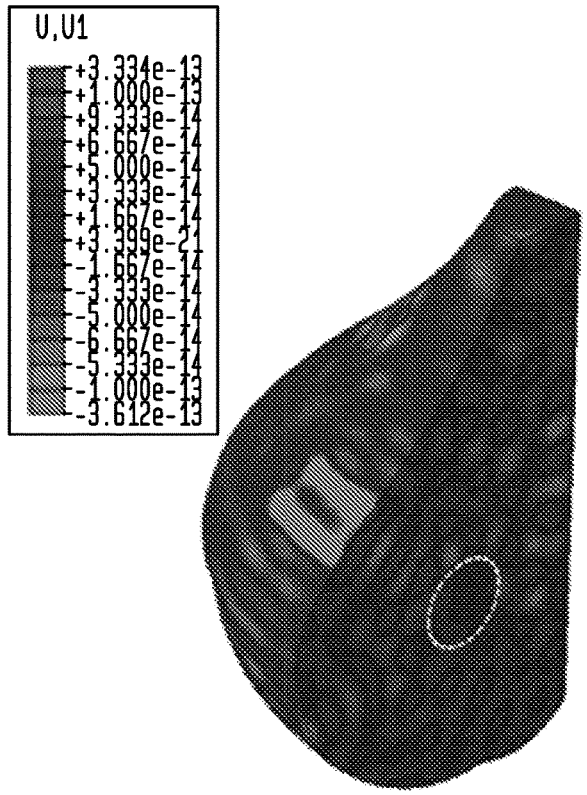
FIG. 4, which consists of portions (a) and (b), illustrates a 3D finite element solid model in Abaqus/CAE of a breast with magnitude displacement field of the complex sinusoidal steady-state solution within an interior plane. Portion (a) illustrates a displacement field in the z-axis for the frequency of operation of 450 Hz, and portion (b) is a similar illustration for 500 Hz, in the background and inclusion (diameter=13 mm) regions.
Figure 4B:
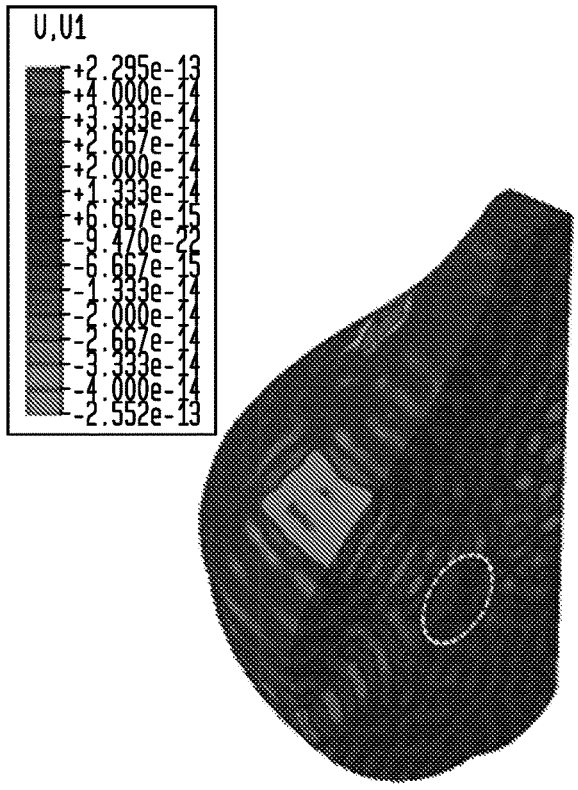

The type of simulation selected was a steady-state dynamic direct solution for two frequencies of operation 450 Hz and 500 Hz. The boundary conditions were set to be zero displacement in the sector that represents the chest wall. In addition, eight surface traction loads were located in different parts of the breast model in order to produce shear displacement at the frequency of operation. The complex values of particle velocity were stored for post-processing. A profile cut of the model shows reverberant vector fields within the background and inclusion for the frequencies of operation of 450 Hz and 500 Hz (FIG. 4(a,b)). In this example, a 3D finite element solid model in Abaqus/CAE of a breast with magnitude displacement field of the complex sinusoidal steady-state solution within an interior plane was used. FIG. 4(a) illustrates a displacement field in the z-axis for the frequency of operation of 450 Hz, and FIG. 3(b) is a similar illustration for 500 Hz, in the background and inclusion (diameter=13 mm) regions.

Experiments have been performed to verify certain aspects of the new approach described above.

Figure 5:
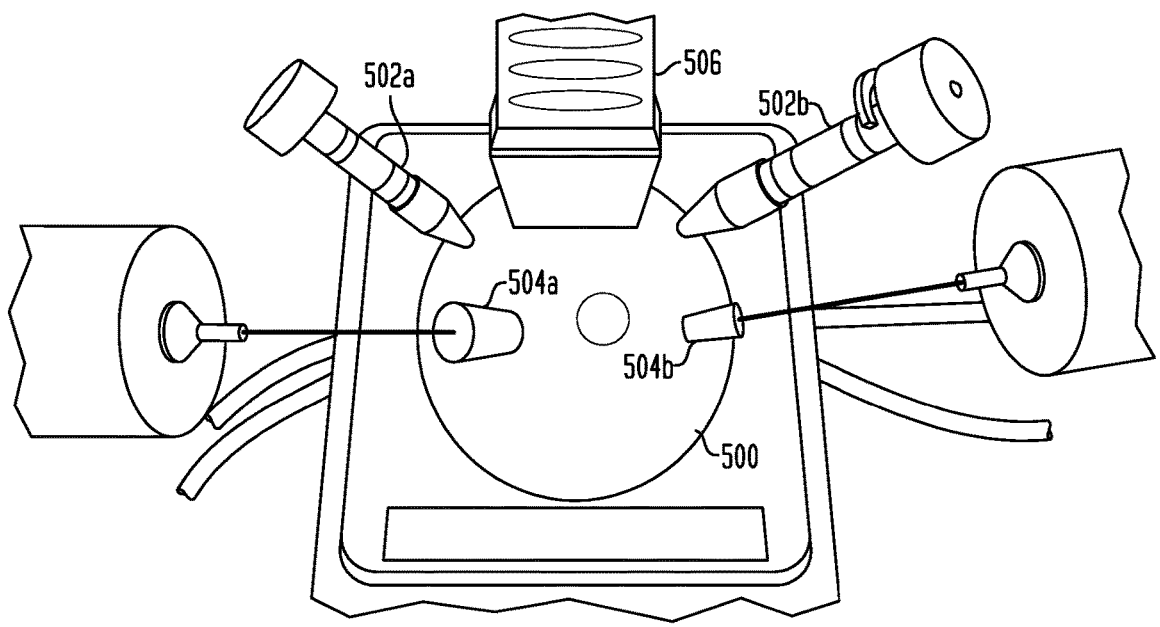
FIG. 5 illustrates an experimental setup using four external vibration sources to generate a reverberation shear wave field inside a phantom simulating breast tissue and an ultrasound transducer measuring motion parameters.

FIG. 5 shows a setup using a zerdine breast phantom 500 in which a reverberant shear wave field is induced by two mechanical vibrators 502a, 502b and two miniature vibration sources 504a, 504b. An imaging ultrasound transducer 506 is a part of an ultrasound imaging system (not seen in the figure). A power amplifier (model 2718, Bruel & Kjaer, Naerum, Denmark), and a digital power amplifier (model LP-2020 A+, Lepai, Bukang, China) driven by a dual channel function generator (model AFG3022B, Tektronix, Beaverton, Oreg., USA) provided input signals to the two mechanical vibration sources (model 4810, Bruel & Kjaer, Naerum, Denmark), and the two miniature vibration sources (model NCM02-05-005-4 JB, H2W, Linear Actuator, Santa Clara, Calif., USA) vibrating at frequencies between 400 and 500 Hz in contact with a gelatin-based and a zerdine breast phantom. A stiffer cylindrical inclusion 12.6 mm in diameter, embedded in an otherwise homogeneous background, was constructed following the procedure used by Hah et al. (2012). One phantom with gelatin (300 Bloom Pork Gelatin, Gelatin Innovations Inc., Schiller Park, Ill., USA) concentrations of 4% for the background and 7% for the inclusion, was created by heating a mixture of gelatin, 0.71 of degassed water, 6.3 g of Na—Cl and 1.05 g of agar to 50° C. The mixture was then cooled to approximately 30° C. and poured into a cubic mold (14×10×10 cm³) and was then allowed to rest at 4° C. overnight. Before the experiment, this phantom was taken out of its molds and left at room temperature for 3 hours. The size and shape of the zerdine phantom simulates a patient in the supine position, and it contains several solid masses that are at least two times stiffer than the background. Lesions range in size from 3 to 10 mm in diameter and are randomly positioned throughout the background. Additionally, a Verasonics ultrasound system (V-1, Verasonics Inc., Kirkland, Wash., USA), which enables high frame rate acquisition and a coherent plane wave compounding acquisition scheme, and a linear array ultrasound transducer 506 (Model L7-4, Verasonics Inc., Redmond, Wash., USA) were used to track the induced displacements using Loupas' estimator (Loupas et al., 1995). A 3-D matrix of IQ data was stored for post-processing. A movie of average axial displacement is computed from the acquired 3-D IQ data. In all the experiments the center frequency was 5 MHz and the tracking pulse repetition frequency (PRF) is set to acquire at least 20 samples per cycle, i.e., PRF=20 times the vibration frequency.

For the gelatin-based phantom materials, compression tests were performed on three cylindrical samples (approximately 38 mm in diameter and 33 mm in length) made with the same mixtures used to construct the gelatin-based media. A QT/5 mechanical device (MTS Systems Co., Eden Prairie, Minn., USA) with a 5 N load cell was used to measure the stress-strain response. The compression rate was adjusted to 0.5 mm/s. These conventional mechanical measurements were considered the reference when assessing the elasticity properties of the cylindrical phantom.

Results from the numerical simulations and experiments are discussed below.

Figure 6B:
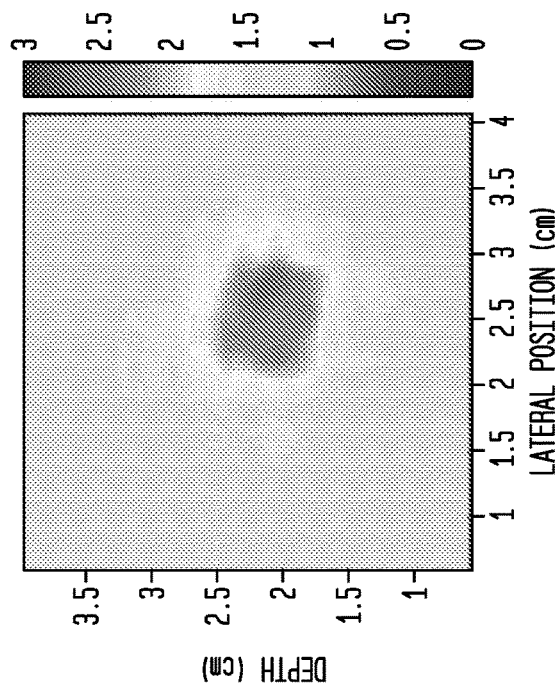
FIG. 6 consists of portions (a) through (d), where (a) illustrates a displacement pattern at 400 Hz obtained using shell-element simulation model in Abaqus/CAE, (b) illustrates a shear wave speed map calculated from (a) using a second moment algorithm, and (c) and (d) illustrate auto correlation pattern extracted from (b) in the x- and y-axis, respectively.
Figure 6D:
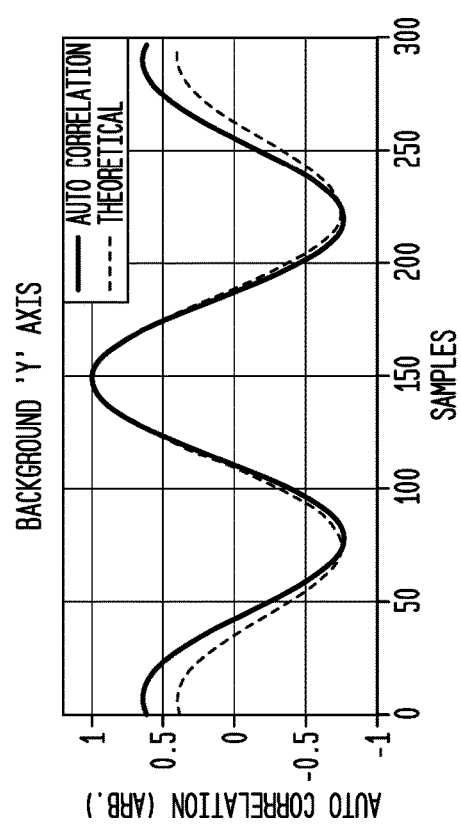
Figure 6A:
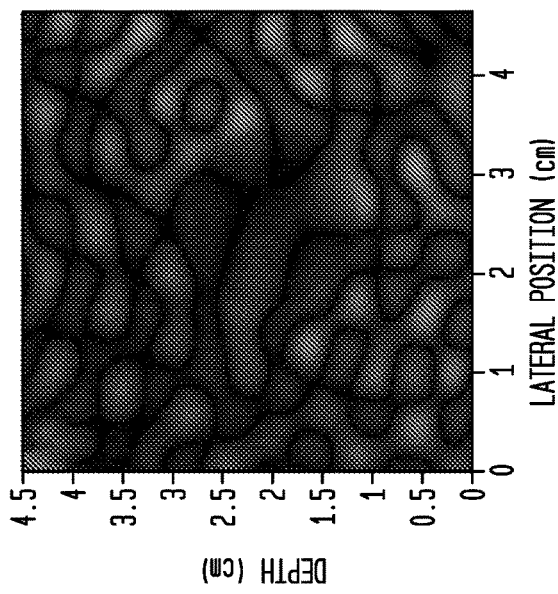
Figure 6C:
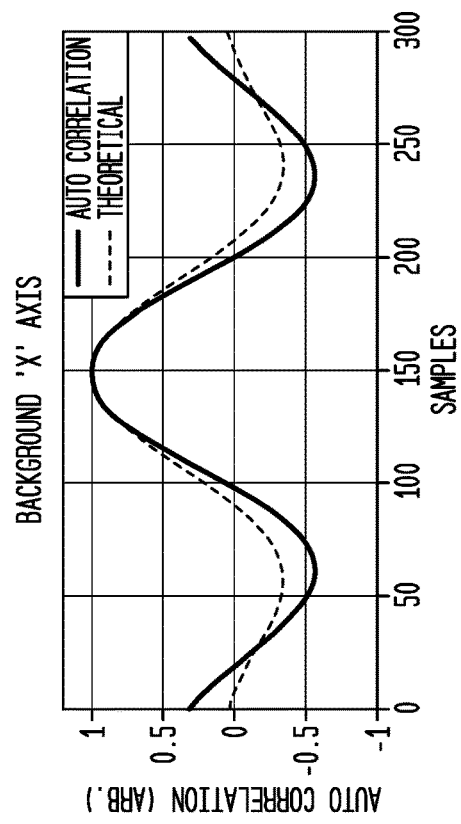

Shell-element analysis results: Complex-value displacement frames of the reverberation pattern within an anterior ROI containing the lesion were stored for analysis. FIG. 6(a) shows the real part of the displacement pattern for an excitation frequency of 400 Hz in which the background and inclusion can be identified by the global separation size of the peaks and valleys of the interference. FIG. 6(b) shows a 2D shear wave speed (SWS) map obtained by applying the new approach to an autocorrelation window ($1.3 \times 1.3$ cm$^2$) which is moved to cover the entire ROI. Profiles in the x and y direction are taken from the 2D cross correlation, which are in good agreement with theory when compared to the equations (17) and (18) in FIG. 6(c,d), respectively. Subsequently, the second moment approach described in equation (23) is applied to the correlation profiles taking into account the scale factor C obtained previously from simulations. The estimation of $\hat{k}$ in both axes is averaged and used in the calculation of the shear wave speed by $c_s = \omega/\hat{k}_{ave}$.

Figure 7A:
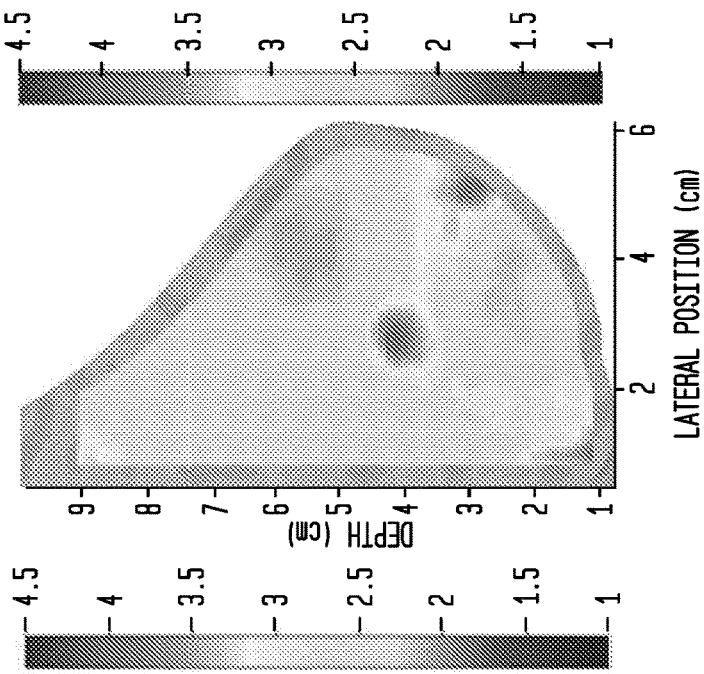
FIG. 7 consists of portions (a) through (c), where (a) illustrates a 2D profile of the 3D displacement pattern of a breast interior at 450 Hz, obtained using Abaqus/CAE, and (b) and (c) illustrate a shear wave speed map obtained from (a) using a second moment algorithm for frequencies of 450 Hz and 500 Hz, respectively.
Figure 7B:
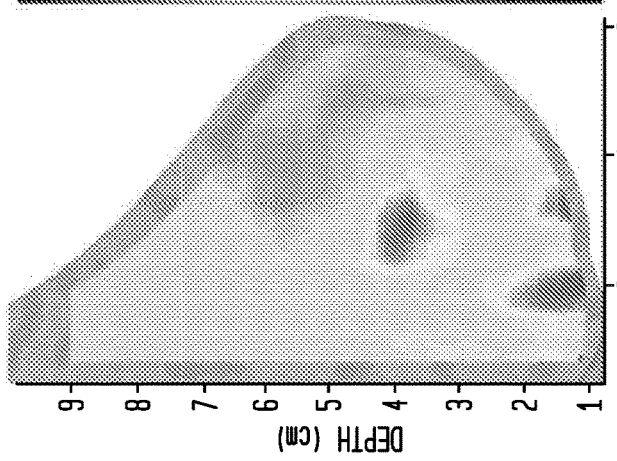
Figure 7C:
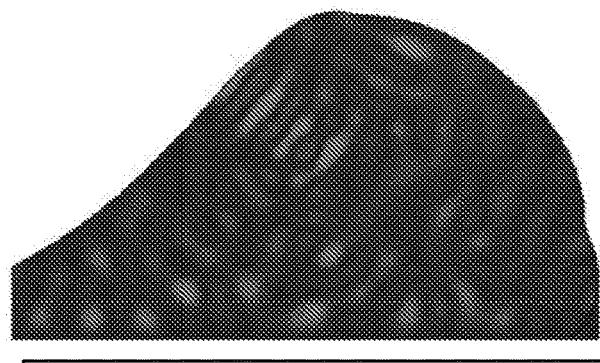

3-D solid finite element analysis results: Complex-value displacement frames of the reverberation at 450 Hz and 500 Hz were obtained during simulations. FIG. 7(a) shows a profile of the real part of the displacement pattern for 450 Hz excitation frequency. The effects of the viscosity (attenuation) and the boundary conditions influence the quality of the reverberation pattern. The same approach for the calculation of SWSM on the shell-element simulation data is applied for the 3D finite element case as shown in FIG. 7(b,c). Average values of shear wave speed reports $c_s = 2.45 \pm 0.1$ m/s in the background (ground truth $c_s = 2.58$ m/s) and $c_s = 3.49 \pm 0.26$ m/s in the inclusion (ground truth $c_s = 3.65$ m/s). Some artifacts are seen near the outer boundaries where the assumptions of the isotropic reverberant fields may not hold.

Ultrasound experiments results when using the Gelatin-based phantom: FIG. 8(a) shows the reverberation displacements from the gelatin-based phantom at 400 Hz. FIG. 8(b) presents the phase map obtained by the Fourier transform of the displacement pattern through time at each (axial-lateral) location. The B-mode and the SWS images (obtained by applying the new approach to a window $1.3 \times 1.3$ cm$^2$ in size) are shown in FIG. 8(c,d), respectively. A region of interest ($7 \times 7$ mm$^2$) was taken from the background and the inclusion in order to obtain a mean value of each region: $1.22 \pm 0.01$ m/s, $2.15 \pm 0.13$ m/s, respectively. The SWS result for both regions are in agreement with the elasticity properties obtained with mechanical measurements: $1.32 \pm 0.16$ m/s, $2.46 \pm 0.21$ m/s, respectively. Finally, FIG. 8(e) shows the SWS profile for a fixed depth corresponding to FIG. 8(d).

Ultrasound experiments results when using the Zerdine breast phantom: FIG. 9 shows the reverberation results from the CIRS breast phantom. The displacement patterns using a vibration frequency of 450 Hz is shown in FIG. 9(a). FIG. 9(b) presents the phase map of the reverberation pattern at 450 Hz; it can be noticed that there are two different wavelengths between 2 and 3 cm in the axial direction, which is the region where the inclusion is located (see B-mode image (FIG. 9(c)). The SWS maps, (obtained by applying our approach to a correlation window $1.3 \times 1.3$ cm$^2$ in size) overlaying the B-mode image, are shown in FIG. 9(d). A region of interest ($7 \times 7$ mm$^2$) was taken from the background and the inclusion in order to obtain a mean value for each region: $2.28 \pm 0.14$ m/s, $3.43 \pm 0.18$ m/s for 450 Hz, respectively. The SWS result for the background is in agreement with the elasticity properties specified by the CIRS manufacturer: $2.58 \pm 0.32$. For the SWS result at the inclusion, the phantom manufacturer only reported that the inclusion stiffness is, at least, two times higher than the background. Thus, the SWS result for the inclusion is in agreement with that information as well. Finally, FIG. 9(e) shows the SWS profile for a fixed depth corresponding to FIG. 9(d).

Figure 10A:
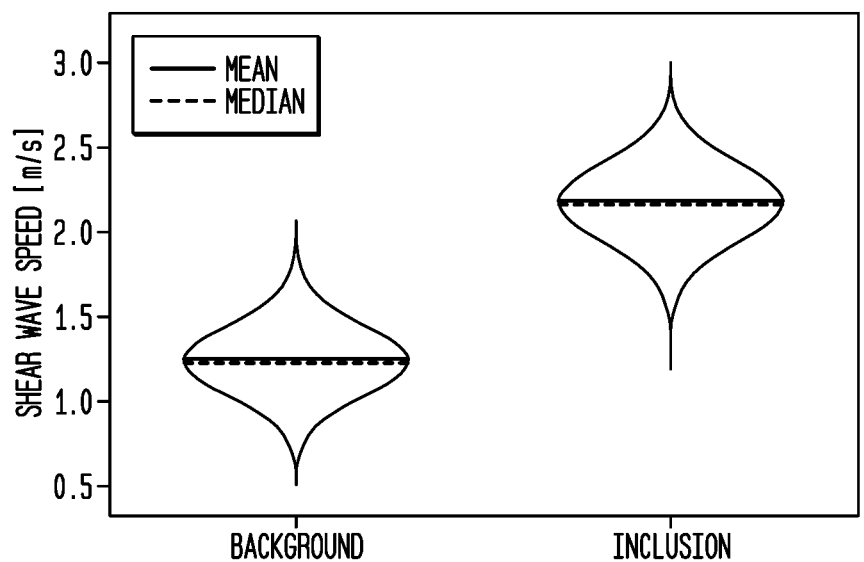
FIG. 10 illustrates violin plots showing the SWS estimate summary for the background and inclusion ROI and consists of portions (a) and (b) that show an SWS summary for the gelatin-based phantom at 400 Hz and a zerdine breast phantom at 450 Hz, respectively.
Figure 10B:
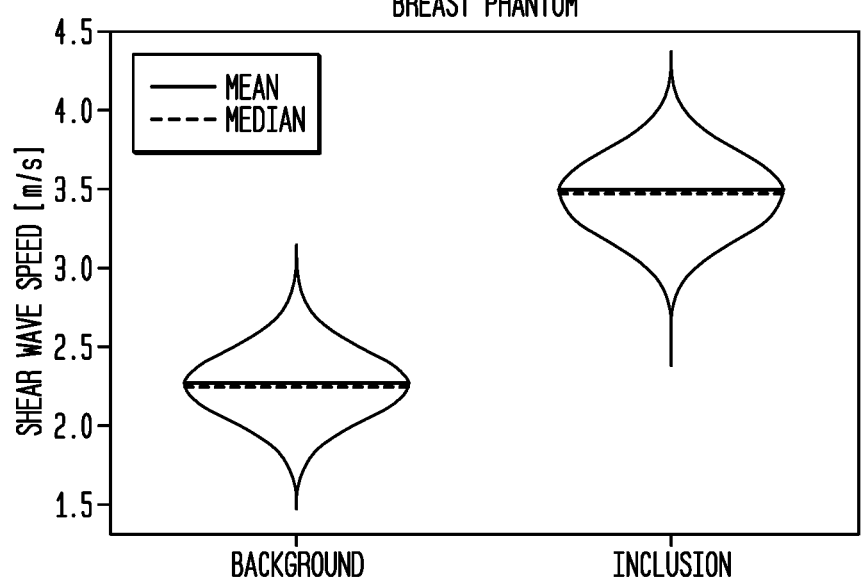

FIG. 10 shows a SWS estimate summary, background and inclusion ROI for the gelatin-based and breast phantoms in portions (a) and (b) respectively. The width of the violin plots shows the probability density of the data at different values. The solid and dashed lines represent the mean and median of the data.

One example of a practical implementation of the new approach is described below, but it should be clear that this is one of several possible implementations and the new approach is not limited to this example.

As illustrated in block diagram form in FIG. 11, a system 100 comprises a vibration source 102, which in this example is in the form of individual vibration sources 102-1 through 102-N, coupled with a body 104 and configured to produce shear waves that interact with each other and with structures in body 104 to produce a reverberant shear wave field in the body. In other examples, an integrated vibration source 102 can be used, such as an extended surface that moves differently at different points on the surface in a way that produces the required reverberant shear wave field in body 104, and thereby functions similarly to an array of individual vibration sources. Arrows 104b designate randomly or nearly randomly distributed directions of shear waves in the reverberant shear wave field in body 104. An imaging system 106 measures motion of a region of interest (ROI) 104a in body 104, preferably in a single selected direction such as the beam direction of the imaging ultrasound transducer, in the presence of the reverberant shear wave field. An image processor 108 applies computer processing to the motion measurements from imaging transducer 106 and to parameters of the frequency of vibration sources 102 to produce estimates of one or more viscoelastic properties of ROI 104a such as stiffness properties. A computer display 110 displays the estimates and typically also includes an interface 110a through which a user communicates with the system. A controller 112 communicates with elements 102, 106, 108, 110, and 110a to monitor and control their operations.

An important aspect of system 100 is that it only needs to measure motion of ROI in a single direction, and that the shear waves in body 104 typically are in all or nearly all directions. Vibration source 102 can comprise several, typically 3 to 7 or more individual sources or points from which shear waves are emitted, arrayed around body 104 in a way that need not be precise so long as they can contribute to produce the specified reverberant shear wave field. The shear waves that source 102 produces need not be precisely directed. Individual vibration sources 102 can be used that operate independently of each other, or one or more integrated set or sets of sources 102 can be used. To generalize in the case of using individual vibration sources, vibration sources 102-1 through 102-N are used, where N is a positive integer greater than 1 and preferably greater than 2. In the case of an integrated vibration source, the source has 1 through N points or portions that produce respective shear waves that in turn produce the required reverberant field. Imaging system 106 can include an ultrasound transducer with a 1D or 2D array of transducer elements operating at a frequency suited to imaging the region of interest, such as 5 MHz or another suitable frequency. As another example, imaging system 106 can use another imaging modality such as magnetic resonance, in which case the required imaging pulse sequence is simplified and is faster than for 2D or 3D MR imaging because only motion of ROI 104a in a single direction is required to be measured. As another example, imaging system 106 can employ Optical Coherence Tomography (OCT) or x-ray imaging. The images should be taken at the required time sequence frequency, for example two times or preferably more, such as five times or ten times, the highest frequency of interest of the reverberant shear wave field in the region of interest in the body. Image processor 108 can be a known ultrasound engine adapted to process the echoes from the ultrasound transducer into images that can be autocorrelated to derive displacement of ROI 104a and speed of the displacements in a selected direction, and thereafter the desired one or more viscoelastic properties of the ROI. In case imaging transducer 106 is a magnetic resonance scanner, image processor 108 can be the known computer facility of the MRI system, also adapted to provide measurements of displacement of ROI 104a and ultimately the desired one or more viscoelastic properties. In the case of OCT or x-ray imaging, image processor 108 can be the existing system's computer programmed to provide the images of the ROI from which can be derived the measurements of displacement and ultimately the desired viscoelastic properties. Computer display 110 can be the display that typically is a part of an ultrasound, MRI or OCT scanner or an x-ray imaging system. Controller 112 can be a separate device serving the indicated functions of can be implemented by suitably programming and interfacing an existing computer facility of an ultrasound or MM or OCT scanner or x-ray imaging system.

In operation, a body 104 such as a patient's breast is placed on a platform 114 that is equipped with vibration a vibration source 102 such as individual sources 102-1 through 102-N, for example 3-7 or more sources, that are coupled with breast 104 to create a reverberant shear wave field in it. The vibration sources can be on the platform, on a separate structure, or in a belt that can surround a patient's abdomen, or in some other integrated structure, so long as a sufficient area of body 104 is free to couple an imaging ultrasound transducer to the patient that can image the ROI and can induce the required reverberant filed body 104. In the case MM is used to image the ROI, suitable precautions need to be taken to account for the presence of a strong steady magnetic field and magnetic gradients in selecting and using the vibration sources and in their placement relative to the patient's body and MRI components such as RF coils. Other imaging modalities can be used instead of ultrasound and MM, such as OCT (Optical Coherence Tomography) or x-ray imaging so long as they can produce the required time sequence of images of the ROI that show its motion in the presence of the reverberant shear wave field.

Figure 12:
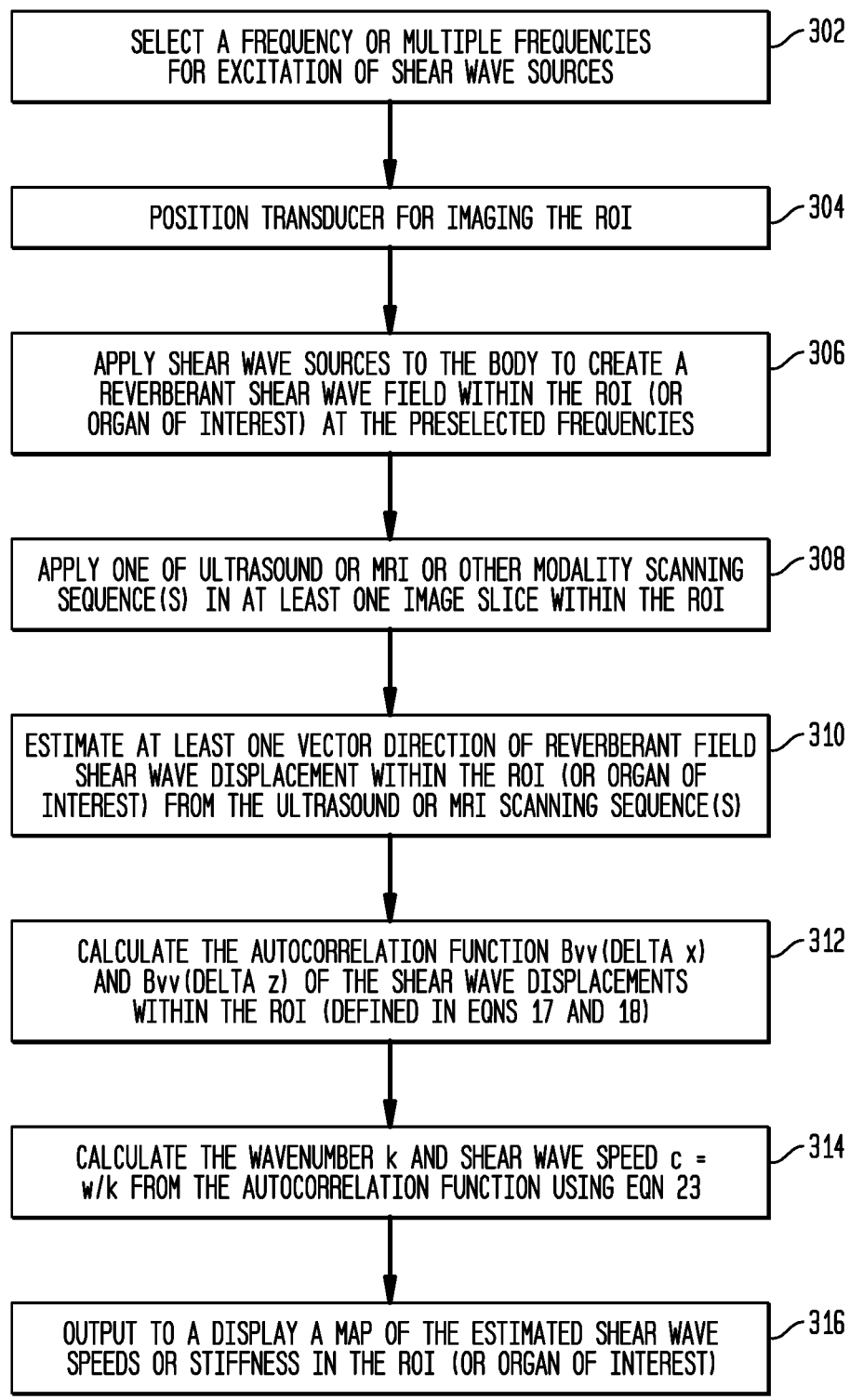
FIG. 12 is a flow chart of a process for estimating parameters such as stiffness of a region of interest using an example of the approach described in this patent specification.

Main steps of the process are illustrated in FIG. 12. In step 302, a user such as a health professional selects a frequency of the shear waves, or a frequency band, and inputs the selection into controller 112 through interface 110a. The selected frequency preferably is in the range of 30-1000 Hz, and can be 500 Hz as one example, but can be a different range, such as without limitation 1600-2400 Hz, or 1000-4000 Hz, for example when assessing bone in the patient may be of interest. Alternatively, the frequency or frequency range or ranges can be pre-set or otherwise communicated to the vibration source or sources so that the user need not input them for each patient study. Even if pre-set, the system can still allow the user to over-ride the preset and select a different vibration frequency or band or bands for a given patient study. Preferably the vibration source produces shear waves that have substantially the same frequency, or frequencies that are in a narrow band within a wider band such as 30-1000 Hz or another relatively wide range such as 1600-2400 Hz, or 1000-4000 Hz, but it is possible to produce shear waves that differ substantially in frequency and/or phase from each other, in which case the processing of the images of the ROI needs to take into account such substantial difference. In step 304, the user images the ROI, for example by moving an ultrasound transducer that is a part of imaging system 106 over breast 104, and observes the resulting images to select a position and an orientation of the transducer in which the ROI is within the image. For this purpose, the user can operate a commercially available ultrasound system such as those offered by GEHealthcare under the tradename LOGIQ, by Siemens (Acuson) offered under the tradename S3000, or another commercially available ultrasound scanner or a scanner purpose-designed specifically for system 100 of FIG. 11. Such an ultrasound scanner includes an ultrasound transducer serving as an element of imaging system 106, an ultrasound engine serving as element 108, and a display and interface serving as elements 110 and 110a illustrated in FIG. 12. In step 306, the user turns on vibration source or sources 102 to produce the required reverberant shear wave field in breast 104 or at least at ROI 104a and surroundings. While the reverberant shear wave field is present in breast 104 or at least at ROI 104a and surroundings, in step 308 the ultrasound scanner continues to image ROI 104a to produce a rapid time sequence of images of the ROI. Image processor 108 receives from imaging system 106 the required images and in step 310 estimates at least one vector direction of the reverberant shear waves, Image processor 108, which can be the ultrasound engine of the indicated commercially available ultrasound scanners, programmed as needed to carry out the operations described in this patent specification, receives as inputs the vibration frequency of sources 102 and the vector estimate in step 310, and in step 312 computes the autocorrelation functions $Bv_x v_x (\Delta t, \Delta \varepsilon_z)$ and $Bv_x v_x (\Delta t, \Delta \varepsilon_x)$ identified in equations (17) and (18), respectively, using known autocorrelation algorithms to convert the measured displacements into the autocorrelation values. (Autocorrelations can be taken along one or more other $\Delta \varepsilon$ lines, instead of or in addition to taking autocorrelation along the $\Delta \varepsilon_z$ and $\Delta \varepsilon_x$ directions, for example along a diagonal line between the x and z axes or along some other direction that is not the direction of the imaging ultrasound beam or perpendicular to the beam.) For this purpose, step 312 uses the displacements for increments $\Delta t$ and $\Delta \varepsilon_z$ from step 310. In step 314, image processor 108 computes an estimate of the wave number k and the shear wave speed c=w/k from the autocorrelation function per equation 23. In step 316, the system outputs to a computer display a map of the estimates shear wave speeds and/or viscoelastic parameters such as stiffness of the ROI or the organ of interest.

In principle, the calculation of the indicated autocorrelation functions $Bv_x v_x (\Delta t, \Delta \varepsilon_z)$ and $Bv_x v_x (\Delta t, \Delta \varepsilon_x)$ identified in equations (17) and (18) involves matching positions of the ROI or points of the ROI in successive ultrasound or MR or OCT images of the ROI and surroundings to determine how those positions have changed in shape or position from one point in time to another along the x-direction and/or along the z-direction in this example, and thus estimate motion in one or more directions of the ROI or points thereof. $Bv_x v_x$ ($\Delta t, \Delta \varepsilon$) pertains to motion in the z-direction, for example perpendicular to the imaging beam from the ultrasound transducer, and $Bv_x v_x$ ($\Delta t, \Delta \varepsilon_x$) pertains to motion in the x-direction, for example along the direction of the beam from the ultrasound transducer. Conventional processing, within the skill of an ordinary computer programmer, can be used to obtain the $\Delta t$, $\Delta \varepsilon_z$, and $\Delta \varepsilon_x$ values from the succession of images of the ROI and use them to calculate the autocorrelation values and in turn use the calculated autocorrelation values in equation 23. See Loupas, 1995 for an example of autocorrelation processing. While autocorrelation along only one direction is in principle sufficient to derive the desired elastic property or properties of the ROI, such as stiffness or speed, in practical applications taking autocorrelation along two or even more directions may produce benefits such as reduction of noise effects resulting from redundancy of measurements. Once at least one of the autocorrelation values is available, equation (23) explains how to use it to derive the k (wave number) estimate. The coefficient C in equation (23) is empirically derived by tests with a known object such as a breast phantom where the parameters of equation (23) other than C are known or can be estimated, and solving for C. Stiffness is related to wave number k, as explained for example in Parker 2011, and can be derived for each point of interest in the ROI to estimate and display stiffness at a single point in the ROI, of as a 2D map of points in the ROI, or as a 3D map of points.

In review, there are several advantages to utilizing the framework of reverberant fields. First, the presence of reflections from boundaries and internal inhomogeneities is unavoidable in some common elastographic approaches, and these reflections plus the application of multiple sources and mode conversions can all contribute to the creation of the reverberant shear wave field. Once established, the characteristics of that field can be exploited to estimate the underlying shear wave phase velocity and/or viscoelastic properties. Secondly, the expected value of the autocorrelation function has been derived assuming only one vector component of detected velocity. This represents the simplest and most rapid data acquisition for both ultrasound and MRI, as additional transmit directions (in ultrasound) or additional phase encoding (in MRI) are required to determine additional vector components of shear wave velocity, and these are unnecessary in the framework developed herein. Thirdly, the need to verify a principal direction of wave propagation is eliminated in the reverberant framework as the underlying mathematics account for a superposition of waves. Fourthly, the need for explicit knowledge of boundary conditions or second derivatives that are essential in some inverse approaches (Doyley, 2012) are avoided in the reverberant approach.

Factors such as organ size, attenuation, frequency, and shear wave sources can cause degradation or deviation from the model. In addition, the performance of estimators of shear wave speed as a function of the same parameters can requires a more detailed assessment. Finally, multi-frequency versions of the new approach can be implemented to assess the frequency dependence of shear wave speed and hence the dispersion and viscoelastic properties.

This patent specification describes an alternative to the known approaches discussed above, and involves applying a narrow-band reverberant field of many waves within tissue. These waves are naturally established (even unavoidable) in practical situations, and can be reinforced by utilizing multiple shear sources near the tissues of interest. This new approach leads to simpler solutions, more facile implementation, and rapid estimation of local tissue shear wavelength or shear wave speed and thus stiffness or elasticity.

REFERENCES

Abramowitz M and Stegun I A 1964 *Handbook of mathematical functions with formulas, graphs, and mathematical tables* (Washington: U.S. Govt. Print. Off.)

Baddour N 2011 Multidimensional wave field signal theory: mathematical foundations *AIP Advances* 1 0221201-02212024

Bracewell R N 1965 *The Fourier transform and its applications* (New York: McGraw-Hill)

Brum J, Catheline S, Benech N and Negreira C 2015 Quantitative shear elasticity imaging from a complex elastic wavefield in soft solids with application to passive elastography *IEEE Trans Ultrason Ferroelectr Freq Control* 62 673-85

Catheline S, Benech N, Brum J and Negreira C 2008 Time reversal of elastic waves in soft solids *Physical review letters* 100 064301

Cook R K, Waterhouse R V, Berendt R D, Edelman S and Thompson M C 1955 Measurement of correlation coefficients in reverberant sound fields *J Acoust Soc Am* 27 1072-7

Deffieux T, Gennisson J L, Bercoff J and Tanter M 2011 On the effects of reflected waves in transient shear wave elastography *IEEE Trans Ultrason Ferroelectr Freq Control* 58 2032-5

Doyley M M 2012 Model-based elastography: a survey of approaches to the inverse elasticity problem *Phys Med Biol* 57 R35-R73

Engel A J and Bashford G R 2015 A new method for shear wave speed estimation in shear wave elastography *IEEE Trans Ultrason Ferroelectr Freq Control* 62 2106-14

Fai Y, Levinson S F, Dongshan F and Parker K J 1998 Feature-adaptive motion tracking of ultrasound image sequences using a deformable mesh *IEEE Trans Med Imaging* 17 945-56

Fu D, Levinson S F, Graceswki S M and Parker K J 1999 Solution of the inverse problem in sonoelastography using an iterative forward approach. In: *Ultrasonic Imaging and Tissue Characterization Symposium*, pp 61-2

Gallot T, Catheline S, Roux P, Brum J, Benech N and Negreira C 2011 Passive elastography: shear-wave tomography from physiological-noise correlation in soft tissues *IEEE Trans Ultrason Ferroelectr Freq Control* 58 1122-6

Hah Z, Hazard C, Mills B, Barry C, Rubens D and Parker K 2012 Integration of Crawling Waves in an Ultrasound Imaging System. Part 2: Signal Processing and Applications *Ultrasound Med Biol* 38 312-23

Loupas T, Peterson R B and Gill R W 1995 Experimental evaluation of velocity and power estimation for ultrasound blood flow imaging, by means of a two-dimensional autocorrelation approach *IEEE Trans Ultrason Ferroelectr Freq Control* 42 689-99

Manduca A, Lake D S, Kruse S A and Ehman R L 2003 Spatio-temporal directional filtering for improved inversion of MR elastography images *Med Image Anal* 7 465-73

McLaughlin J and Renzi D 2006 Shear wave speed recovery in transient elastography and supersonic imaging using propagating fronts *Inverse Probl* 22 681-706

Oliphant T E, Manduca A, Ehman R L and Greenleaf J F 2001 Complex-valued stiffness reconstruction for magnetic resonance elastography by algebraic inversion of the differential equation *Magn Reson Med* 45 299-310

Parker K J 2013 *Imaging in medical diagnosis and therapy*, (Boca Raton, Fla.: CRC Press) pp xvii, 331 p.

Parker K J, Doyley M M and Rubens D J 2011 Imaging the elastic properties of tissue: the 20 year perspective *Phys Med Biol* 56 R1-R29

Parker K J and Lerner R M 1992 Sonoelasticity of organs: shear waves ring a bell *J Ultrasound Med* 11 387-92

Parker K J and Maye B A 1984 Partially coherent radiation from reverberant chambers *J Acoust Soc Am* 76 309-13

Parker K J, Taylor L S, Gracewski S and Rubens D J 2005 A unified view of imaging the elastic properties of tissue *J Acoust Soc Am* 117 2705-12

Pengfei S, Heng Z, Manduca A, Urban M W, Greenleaf J F and Shigao C 2012 Comb-push ultrasound shear elastography (CUSE): a novel method for two-dimensional shear elasticity imaging of soft tissues *IEEE Trans Med Imaging* 31 1821-32

Pierce A D 1981 *McGraw-Hill series in mechanical engineering*, (New York: McGraw-Hill Book Co.)

Ringleb S I, Chen Q, Lake D S, Manduca A, Ehman R L and An K N 2005 Quantitative shear wave magnetic resonance elastography: comparison to a dynamic shear material test *Magn Reson Med* 53 1197-201

Romano A J, Bucaro J A, Ehnan R L and Shirron J J 2000 Evaluation of a material parameter extraction algorithm using MRI-based displacement measurements *IEEE Trans Ultrason Ferroelectr Freq Control* 47 1575-81

Roux P, Sabra K G, Kuperman W A and Roux A 2005 Ambient noise cross correlation in free space: theoretical approach *J Acoust Soc Am* 117 79-84

Sinkus R, Lorenzen J, Schrader D, Lorenzen M, Dargatz M and Holz D 2000 High-resolution tensor MR elastography for breast tumour detection *Phys Med Biol* 45 1649-64

Taylor L S, Porter B C, Rubens D J and Parker K J 2000 Three-dimensional sonoelastography: principles and practices *Phys Med biol* 45 1477-94

Tzschatzsch H, Guo J, Dittmann F, Hirsch S, Barnhill E, Johrens K, Braun J and Sack I 2016 Tomoelastography by multifrequency wave number recovery from time-harmonic propagating shear waves *Med Image Anal* 30 1-10

Tzschatzsch H, Ipek-Ugay S, Guo J, Streitberger K J, Gentz E, Fischer T, Klaua R, Schultz M, Braun J and Sack I 2014 In vivo time-harmonic multifrequency elastography of the human liver *Phys Med Biol* 59 1641-54

Tzschatzsch H, Ipek-Ugay S, Trong M N, Guo J, Eggers J, Gentz E, Fischer T, Schultz M, Braun J and Sack I 2015 Multifrequency time-harmonic elastography for the measurement of liver viscoelasticity in large tissue windows *Ultrasound Med Biol* 41 724-33

Van Houten E E, Miga M I, Weaver J B, Kennedy F E and Paulsen K D 2001 Three-dimensional subzone-based reconstruction algorithm for MR elastography *Magn Reson Med* 45 827-37

The invention claimed is:

1. A system using a reverberant shear wave field in a body to estimate viscoelastic properties of hidden regions of interest in the body, comprising:
   a vibration source configured to produce plural shear waves at selected frequencies, selected locations, and selected orientations and operating in a manner that, when actuated, produces shear waves that interact with each other and with structures in the body to produce a reverberant shear wave field in the body;
   an imaging device configured to measure motion of a region of interest in the body in a first selected direction in the presence of said reverberant shear wave field and to produce an estimate of the measured motion;
   an image processor configured to receive as inputs the selected frequencies of the shear waves and said estimate of measured motion, and to process the inputs with computer algorithms to provide an estimate of one or more viscoelastic properties of said region of interest in the body;
   a computer display configured to display said estimate of said one or more viscoelastic properties of the region of interest; and
   a controller configured to actuate the vibration source and operatively coupled with said imaging device, image processor, and computer display to control their operation.

2. The system of claim 1, in which the imaging device is an ultrasound scanner that includes an ultrasound transducer and is configured to provide a time sequence of ultrasound images of the region of interest and said estimate of measured of motion.

3. The system of claim 1, in which the imaging device is a magnetic resonance imaging (MRI) machine configured to provide a time sequence of magnetic resonance images of the region of interest and said estimate of measured motion.

4. The system of claim 1, in which the imaging device is an Optical Coherence Tomography (OTC) system configured to provide a time sequence of OTC images of the region of interest and said estimate of measured motion.

5. The system of claim 1, in which the imaging device is an x-ray imaging system configured to provide a time sequence of x-ray images of the region of interest and said estimate of measured motion.

6. The system of claim 1, in which the vibration source produces shear waves at one or more frequencies in the range of 30-1000 Hz.

7. The system of claim 1, in which the vibration source produces shear waves at one or more frequencies in the range of 1600-2400 Hz.

8. The system of claim 1, in which the vibration source produces shear waves at one or more frequencies in the range of 1000-4000 Hz.

9. The system of claim 1 in which the vibration source comprises 3-7 individual vibration sources.

10. The system of claim 1 in which the vibration source comprises more than 7 individual vibration sources.

11. The system of claim 1 in which the vibration source is an extended vibration surface.

12. The system of claim 1, in which said estimate of measured motion includes a position in said first selected direction of the region of interest at plural respective times and speed of the change in position in said first selected direction, and the image processor is configured to take images of the region of interest and calculate said one or more estimates as a function of auto-correlation of said images.

13. The system of claim 1, in which the imaging device is further configured to measure motion in a second selected direction and provide an estimate of the measured motion in the second direction.

14. The system of claim 1, in which the image processor is configured to provide a map of said one or more viscoelastic properties of each of plural points within the region of interest.

15. The system of claim 1, in which the image processor is configured to provide a two-dimensional map of said one or more viscoelastic properties of each of plural points within the region of interest.

16. The system of claim 1, in which the image processor is configured to provide a three-dimensional map of said one or more viscoelastic properties of each of plural points within the region of interest.

17. A method of using a reverberant shear wave field in a body to estimate viscoelastic properties of hidden regions of interest in the body, comprising:
producing plural shear waves at selected frequencies that interact with each other and with structures in the body to produce a reverberant shear wave field in the body;
using an imaging device to image a region of interest in the body in the presence of said reverberant shear wave field and to produce an estimate of motion of the region of interest in a selected first direction;
computer processing a measure of the selected frequencies of the shear waves and said estimate of measured motion to provide an estimate of one or more viscoelastic properties of said region of interest in the body;
displaying said estimate of one or more viscoelastic properties of the region of interest on a computer display; and
interacting with said steps of producing shear waves, imaging, computer processing, and computer display to control their operation.

18. The method of claim 16, in which the step of using an imaging device comprises using an ultrasound scanner to produce said time sequence of ultrasound images of the region of interest and said estimate of motion.

19. The method of claim 17, in which the step of using an imaging device comprises using an MRI scanner to produce said time sequence of ultrasound images of the region of interest and said estimate of motion.

20. The method of claim 17, in which the step of using an imaging device comprises using an Optical Coherence Tomography (OTC) system configured to provide a time sequence of OTC images of the region of interest and said estimate of motion.

21. The method of claim 17, in which the step of using an imaging device comprises using an x-ray imaging system configured to provide a time sequence of x-ray images of the region of interest and said estimate of motion.

22. The method of claim 17, in which the step of using an imaging device further comprises measuring motion of the region of interest in a second selected direction and providing an estimate of the measured motion in the second direction, and the computer processing step comprises using the estimates of motion in both the first and the second direction to provide said estimate of one or more viscoelastic properties.

23. The method of claim 17, in which the computer processing step further comprises providing an estimate of said one or more viscoelasticity properties of each of plural points within the region of interest.

24. The method of claim 17, in which the computer processing step provides a three-dimensional map of said one or more viscoelastic properties of each of plural points within the region of interest.

25. The method of claim 17, in which the step of using an imaging device comprises carrying out autocorrelation of said images to produce said estimate of motion.

* * * * *